(12) United States Patent
Takaoka et al.

(10) Patent No.: US 6,346,253 B2
(45) Date of Patent: *Feb. 12, 2002

(54) PHOTOREACTIVE AGENT CONTAINING PHOTOREACTIVE SEMICONDUCTOR FOR REMOVING HARMFUL MATERIALS

(75) Inventors: Kazuchiyo Takaoka; Michihiko Sato; Yoichiro Azuma; Yasuhiro Aizawa, all of Tokyo (JP)

(73) Assignee: Mitsubishi Paper Mills Limited, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/807,701

(22) Filed: Feb. 28, 1997

(30) Foreign Application Priority Data

Mar. 1, 1996 (JP) .............................. 8-044448

(51) Int. Cl.[7] ........................ A01N 25/00; A01N 25/32; B09B 3/00
(52) U.S. Cl. ..................................... 424/400; 435/262.5
(58) Field of Search ................................ 424/405, 400, 424/406; 435/262.5; 210/600; 252/322

(56) References Cited

FOREIGN PATENT DOCUMENTS

| EP | 0 633 064 | 1/1995 |
|----|-----------|--------|
| EP | 0 792 687 | 9/1997 |
| JP | 59-71316  | 4/1984 |
| JP | 60-127371 | 7/1985 |
| JP | 3-75062   | 3/1991 |
| JP | 7-87891   | 9/1995 |

OTHER PUBLICATIONS

Derwent Abstracts, No. 93–112031/14, 1991.
Patent Abstracts of Japan, C–994, Oct. 12, 1992, vol. 16, No. 490.
T. Inoue et al., "Preparation of Polymeric Microsphere–Silica Hybrid Materials by Alkoxide Process", International Symposium on Polymeric Microspheres, (1991), pp. 181–184.
Derwent Abstr. Nr.: 93:112031/14, (1991).

Primary Examiner—David M. Naff
Assistant Examiner—Deborah K. Ware
(74) Attorney, Agent, or Firm—Foley & Lardner

(57) ABSTRACT

A photoreactive agent is provided for removing harmful materials which comprises a substrate and a layer containing a photoreactive semiconductor and organic fine particles coated with inorganic fine particles which is formed on at least one side of the substrate. A photoreactive agent is provided for removing harmful materials which comprises a substrate, a layer containing a photoreactive semiconductor and a layer containing organic fine particles coated with inorganic fine particles which layers are formed in that order on at least one side of the substrate. A photoreactive agent is provided for removing harmful materials which comprises a substrate, a layer containing a photoreactive semiconductor and a layer containing film-forming inorganic fine particles and a water repellent which layers are formed in that order on at least one side of the substrate. A photoreactive agent is provided for removing harmful materials which comprises a substrate, a layer containing a photoreactive semiconductor, a layer containing film-forming inorganic fine particles and a layer containing a water repellent which layers are formed in that order on at least one side of the substrate. The photoreactive agents for removing harmful materials are excellent in ability to remove harmful materials such as malodor, are water-resistant, are not changed in characteristics over a long period of time, and can easily be produced.

22 Claims, No Drawings

PHOTOREACTIVE AGENT CONTAINING PHOTOREACTIVE SEMICONDUCTOR FOR REMOVING HARMFUL MATERIALS

BACKGROUND OF THE INVENTION

The present invention relates to a photoreactive agent for removing harmful materials comprising at least a photoreactive semiconductor which can decompose and remove harmful materials such as malodorants and environmental pollutants by utilizing the photocatalytic reaction of the photoreactive semiconductor.

With an increase of interest in environmental problems, there has recently been an increasing demand for not only the removal of a low concentration of industrial environmental pollutants such as industrial waste gas and waste water but also the removal of malodors and indoor pollutants in daily life. As an agent for removing a low concentration of such harmful materials, in particular, malodors in daily life, there have been generally used, for example, inorganic adsorbents obtained by compositing activated carbon, silica, alumina, a metal oxide, etc.

A removing method using such an adsorbent, however, involves various problems during its employment, for example, as follows. In proportion as harmful materials are adsorbed on the adsorbent, the adsorbability is gradually decreased. Therefore, when the practical adsorbability is lost, the adsorbent has to be renewed. Accordingly, it is necessary to ascertain the duration of effectiveness of the adsorbability.

On the other hand, a method for removing harmful materials using a photoreactive semiconductor has recently been noted. Japanese Patent Laid-Open No. 61-135669 discloses a method for decomposing sulfur compounds, malodorants by irradiating a photoreactive semiconductor such as zinc oxide with ultraviolet light. Japanese Patent Examined Publication No. 2-62297 discloses a method for removing a low concentration of nitrogen oxides by using a mixture of a titanium oxide and activated carbon. Since the decomposition of such malodorants by the photoreactive semiconductor such as a titanium oxide or zinc oxide is caused by oxidative decomposition by positive holes or radicals generated on the surface of the photoreactive semiconductor by the ultraviolet irradiation, materials decomposable by the photoreactive semiconductor are not only organic substances but also sulfides and nitrogen-containing compounds such as ammonia. Moreover, the photoreactive semiconductor itself is not consumed or deteriorated by the decomposition of the malodorants, and its capability is not basically deteriorated so long as its irradiation with ultraviolet light is continued. Thus, the above-mentioned method is markedly advantageous as compared with the case of using only an adsorbent.

The decomposing capability of such photoreactive semiconductors is improved with an increase of their chance of coming into contact with harmful materials, i.e., materials to be decomposed. Therefore, the photoreactive semiconductors are most effective when used in a powder form in which the area of reaction by the contact with the harmful materials is not decreased.

However, powder of the photoreactive semiconductor is not usable as it is in practice. Moreover, in general, the photoreactive semiconductors are not substantially able to form a self-coating film unless at least calcined. Accordingly, for handling the photoreactive semiconductors, they have to be subjected to some processing, for example, employment of a structure-forming agent capable of forming a structural material, together with the photoreactive semiconductors. Japanese Patent Laid-Open No. 3-75062 discloses a photoreactive semiconductor-supporting sheet obtained by supporting a photoreactive semiconductor by the use of a latex having a minimum film-forming temperature of 60° C. or lower.

In general, since latices have a high film-forming capability and are easily dispersible in water, they can easily be applied. However, when the photoreactive semiconductor is mixed with the latex and supported on a sheet according to the above method, a resin contained in the latex is decomposed in itself owing to the powerful oxidative effect of the photoreactive semiconductor. When the photoreactive semiconductor is a titanium oxide or the like which has a particularly high photocatalytic activity, the photoreactive semiconductor-supporting sheet is not fit for long-term use.

In addition, when the photoreactive semiconductor is used for removing harmful materials in the air, its effective photocatalytic capability cannot be obtained because the photoreactive semiconductor surface is coated with the resin, so that direct contact of the harmful materials with the photoreactive semiconductor is remarkably inhibited.

Japanese Patent Laid-Open No. 6-315614 has proposed the following purging agents for purging pollutants from the air or water: a purging agent produced by forming photocatalyst powder composed mainly of a titanium oxide (a photoreactive semiconductor) or a mixture of a titanium oxide and activated carbon into a sheet or a panel by the use of synthetic resin powder, and a purging agent obtained by adhering the same photocatalyst powder as above to the surface of a sheet material or a panel material with an adhesive.

Since a fluororesin such as polytetrafluoroethylene is used as the synthetic resin powder, the former purging agent has a structure hardly attackable by the powerful oxidative effect of the photocatalyst. This purging agent, however, is difficult to process to a large area necessary for cleaning the air, and it involves a problem of environmental pollution due to itself because it cannot be subjected to a discarding treatment such as combustion because of the too high durability of the fluororesin.

In the purging agent obtained by adhering photocatalyst powder with an adhesive, the photocatalyst powder exhibits substantially no photocatalytic capability as in the above when buried in the adhesive, and it is poor in strength as a structural material when merely sticked to the adhesive. Thus, it is impossible to increase the amount of the photocatalyst powder in which the powder acts effectively.

Further, Japanese Patent Laid-Open No. 2-187147 discloses a denitration catalyst obtained by supporting vanadium oxide on solid-supporting paper prepared by impregnating ceramic paper with a mixture of titania sol and silica sol and firing the ceramic paper.

The ceramic paper and silica sol are not photocatalytically attacked by titania sol, and the denitration catalyst is unlikely to cause environmental pollution because of such a structure. However, although a mixed film of titania sol and silica sol is rather good in strength in a dry state, it is poor in water resistance when formed by mere drying. For removing such a defect, an after-treatment such as firing is necessary as described in the above reference, but the fired ceramic paper is poor in flexibility and hence processability.

SUMMARY OF THE INVENTION

An object of the present invention is to provide a photoreactive agent for removing harmful materials which utilizes the photocatalytic capability of a photoreactive semiconductor, is excellent in ability to remove harmful materials such as malodor, is water-resistant, is not changed in characteristics over a long period of time, and can easily be produced.

The present inventors earnestly investigated and consequently have achieved the above object with a photoreactive agent for removing harmful materials which comprises a substrate and a layer containing a photoreactive semiconductor and organic fine particles coated with inorganic fine particles which is formed on at least one side of the substrate.

Basically, the photoreactive agent for removing harmful materials of the present invention is obtained by coating or impregnating a substrate with an aqueous dispersion containing a photoreactive semiconductor and organic fine particles coated with inorganic fine particles. The organic fine particles coated with inorganic fine particles according to the present invention are fine particles obtained by coating the surfaces of organic fine particles with inorganic fine particles by the interaction between the organic fine particles and the inorganic fine particles. Therefore, they are not separated into the inorganic fine particles and the organic fine particles even by dispersion in water.

At the time of film formation by the organic fine particles coated with inorganic fine particles, organic fine particles are thermally fused together with one another through spaces among inorganic fine particles located on the surfaces of the organic fine particles, to form a matrix in a three-dimensional manner. The coating film thus formed is water-resistant and moreover the inorganic fine particles are effectively arranged between the photoreactive semiconductor and the organic fine particles substantially constituting the coating film, so that the organic fine particle component can markedly avoid the strong influence of oxidative decomposition by the photoreactive semiconductor.

More advantageously, the organic fine particles do not completely cover the inorganic fine particles in the formation of the coating film. Therefore, the coating film formed is porous because pores are formed by the inorganic fine particle component of the organic fine particles coated with the inorganic fine particles. Accordingly, the gas-adsorbing properties and the ability to remove harmful materials by light are not greatly inhibited.

The above-mentioned object has been achieved also by a photoreactive agent for removing harmful materials which comprises a substrate, a layer containing a photoreactive semiconductor and a layer containing organic fine particles coated with inorganic fine particles which layers are formed in that order on at least one side of the substrate.

In this photoreactive agent for removing harmful materials, the contact of the photoreactive semiconductor with the organic fine particle component of the organic fine particles coated with inorganic fine particles can be further reduced, so that the deterioration of the coating film over a long period of time is further suppressed. Furthermore, since the strength of coating film of the photoreactive agent for removing harmful materials is determined substantially by the layer containing the organic fine particles coated with inorganic fine particles, increasing the amount of the photoreactive semiconductor, i.e., improving the ability to remove harmful materials by light is possible without greatly deteriorating the strength of the coating film.

The above-mentioned object has been further achieved by the same photoreactive agent for removing harmful materials as above except for further comprising a layer containing a water repellent on the above-mentioned layer containing organic fine particles coated with inorganic fine particles and optionally a photoreactive semiconductor.

This photoreactive agent for removing harmful materials can have a more excellent water resistance in addition to the characteristics described above.

When the inorganic fine particle component of the organic fine particles coated with inorganic fine particles is a metal oxide, it can be prepared on the organic fine particle component prepared or in the granulation for preparing the organic fine particle component. Accordingly, the organic fine particle component and the inorganic fine particle component have a sufficient mechanical strength, so that the organic fine particles coated with inorganic fine particles are not fractured by vigorous stirring for, for example, preparing a solution. In addition, the particle sizes and the like can easily be adjusted.

Furthermore, when the inorganic fine particle component is prepared in the manner described above, a porous coating film can be formed, so that the ability to remove harmful materials by light can be improved.

The above-mentioned object has been still further achieved by a photoreactive agent for removing harmful materials which comprises a substrate, a layer containing a photoreactive semiconductor and a layer containing film-forming inorganic fine particles and a water repellent which layers are formed on at least one side of the substrate.

The film-forming inorganic fine particles can form a coating film because of their film-coating properties, and the layer containing the film-forming inorganic fine particles is porous because pores are formed by the inorganic fine particles.

As in the above, the strength of coating film of the photoreactive agent for removing harmful materials is brought about by the film-forming inorganic fine particles, whereby the amount of the photoreactive semiconductor can be increased without greatly deteriorating the strength of the coating film, and the ability to remove harmful materials by light can be improved.

In addition, water resistance can also be imparted by forming a layer containing a water repellent, as the uppermost layer of the photoreactive agent for removing harmful materials.

During the production of the photoreactive agent for removing harmful materials, the photoreactive semiconductor comes into contact with not only the film-forming inorganic fine particles but also the water repellent. Therefore, when the water repellent is oxidizable, the initial ability to remove harmful materials by light is not sufficient, but after completion of the oxidation of the water repellent on the side on which the photoreactive semiconductor is in contact with the water repellent, the ability to remove harmful materials by light is equal to that attained when the water repellent is not co-used. On the other hand, water-repellent effect is brought about by the unoxidized water repellent present on the side out of contact with the photoreactive semiconductor and hence is not lessened.

The above-mentioned object has been still further achieved by a photoreactive agent for removing harmful materials which comprises a substrate, a layer containing a photoreactive semiconductor, a layer containing film-forming inorganic fine particles and a layer containing a water repellent which layers are formed in that order on at least one side of the substrate.

In this photoreactive agent for removing harmful materials, since the above-mentioned layer containing film-forming inorganic fine particles and a water repellent is replaced by the two layers, i.e., the layer containing film-forming inorganic fine particles and the layer containing a water repellent, the water repellent does not come into contact with the photoreactive semiconductor, so that the ability to remove harmful materials by light is not changed during and after the production irrespective of the oxidation resistance of the water repellent.

In addition, since the water repellent is localized in the surface of the photoreactive agent for removing harmful materials, it can exhibit water resistance more effectively.

In the above-mentioned photoreactive agent for removing harmful materials, when a layer containing film-forming inorganic fine particles is formed between the substrate and the layer containing a photoreactive semiconductor, the substrate does not come into contact with the photoreactive semiconductor because it is isolated therefrom by the film-forming inorganic fine particles. Therefore, the deterioration of the substrate by the photoreactive semiconductor is prevented over a long period of time regardless of the oxidation resistance of the substrate, namely, the deterioration of the photoreactive agent for removing harmful materials is prevented.

When a carrier is incorporated into the layer containing the photoreactive semiconductor by supporting the photoreactive semiconductor on the carrier surface to form larger granules, the leakage and dispersion of the photoreactive semiconductor can be prevented during the production and use and moreover the inactivation of active sites on the surface of the photoreactive semiconductor can be considerably suppressed as compared with an aggregate of the photoreactive semiconductor alone.

Particularly when the aforesaid carrier is a hydrated oxide capable of releasing water owing to heat, the flame retardance of the photoreactive agent for removing harmful materials can be improved.

When a flame retardant is incorporated into the substrate, the flame retardance of the photoreactive agent for removing harmful materials can be further improved.

DETAILED DESCRIPTION OF THE INVENTION

The constituents of the photoreactive agent for removing harmful materials of the present invention are explained below in detail.

The photoreactive agent for removing harmful materials of the present invention comprises a substrate and the following layer or combination of layers formed on at least one side of the substrate: a layer containing at least a photoreactive semiconductor and organic fine particles coated with inorganic fine particles; a combination of a layer containing at least a photoreactive semiconductor and a layer containing at least organic fine particles coated with inorganic fine particles which layers are formed in that order; a combination of the above-mentioned layer(s) and a layer containing a water repellent which is formed on the any of the above-mentioned layers containing at least organic fine particles coated with inorganic fine particles; a combination of a layer containing at least photoreactive semiconductor and a layer containing at least film-forming inorganic fine particles and a water repellent which layers are formed in that order; or a combination of a layer containing at least photoreactive semiconductor, a layer containing at least film-forming inorganic fine particles and a layer containing at least a water repellent which layers are formed in that order.

If necessary, the photoreactive agent for removing harmful materials of the present invention may further comprises a layer containing at least film-forming inorganic fine particles between the aforesaid substrate and the aforesaid layer containing at least a photoreactive semiconductor, may contain a carrier in the layer containing at least a photoreactive semiconductor, or may contain a flame retardant in the substrate.

Further, in the photoreactive agent for removing harmful materials of the present invention, the inorganic fine particle component of the above-mentioned organic fine particles coated with inorganic fine particles is a metal oxide, or the substrate is a hydrated oxide capable of releasing water owing to heat.

The photoreactive semiconductor, the most important component of the photoreactive agent for removing harmful materials of the present invention is a semiconductor which induces photocatalytic reaction and has a forbidden band width of 0.5 to 5 eV, preferably 1 to 4 eV, for example, fine titanium oxide particles, zinc oxide particles, tungsten oxide particles and cerium oxide particles. Of these oxides, titanium oxides are the most suitable for use in life spaces from the viewpoint of its structure stability, ability to remove harmful materials by light, safety in handling, etc., and are advantageously used as the photoreactive semiconductor according to the present invention.

The titanium oxides advantageously usable as the photoreactive semiconductor are industrially produced by hydrolysis of titanyl tetrachloride or titanyl sulfate or vapor phase combustion of titanyl tetrachloride. Metatitanic acid obtained by hydrolyzing titanyl sulfate is an inexpensive and excellent photoreactive semiconductor.

In addition to these production processes, there is a process for producing a titanium oxide from an organic titanate, and this process gives a photoreactive film having high uniformity and transparency.

As other titanium oxides, titanium oxides such as metatitanic acid, orthotitanic acid and hydrous titanium oxide, hydrated titanium oxide, titanium hydroxide [$Ti(OH)_4$], hydroxyl titanium ($Ti(OH)_m X_n$, X is oxygen atom, [m+n=4], etc. may be used as the photoreactive semiconductor according to the present invention.

In the photocatalytic action of the above-exemplified titanium oxide, a reaction induced by radicals generated on the surface plays a principal role. For imparting reducing properties due to electrons more markedly, titanium oxide may be coated with metal fine particles of platinum, gold, vanadium, silver, copper, zinc, rhodium or the like. For imparting reducing properties due to positive holes more markedly, titanium oxide may be coated with a metal oxide such as ruthenium oxide.

The ability of the photoreactive semiconductor to remove harmful materials by light can be effectively attained by increasing the specific surface area of the photoreactive semiconductor to increase the number of generation sites of radicals. Furthermore, when the specific surface area is increased, the contact area per unit amount of the photoreactive semiconductor with the harmful materials is also increased. Therefore, for decomposing the harmful materials, the larger the specific surface area, the more effective the photoreactive semiconductor.

However, when the specific surface area of the photoreactive semiconductor is increased, the cohesive force of the photoreactive semiconductor itself is increased, so that the contact rate of the harmful materials with the photoreactive semiconductor is undesirably decreased. Accordingly, the specific surface area of the photoreactive semiconductor used in the present invention is preferably approximately 10–500 $m^2/g$, more preferably approximately 100–500 $m^2/g$. Particularly when a titanium oxide is used as the photoreactive semiconductor, the specific surface area is preferably approximately 50–400 $m^2/g$, more preferably approximately 100–400 $m^2/g$. The particle size of the photoreactive semiconductor is preferably approximately 3–120 nm, more preferably approximately 3–20 nm.

The content of the photoreactive semiconductor in the layer containing at least the photoreactive semiconductor and organic fine particles coated with inorganic fine particles is not remarkably related to constituents other than the photoreactive semiconductor which constitute the layer, for example, the organic fine particles coated with inorganic fine particles, and is preferably 1 to 50 $g/m^2$, more preferably 2 to 30 $g/m^2$.

When the content of the photoreactive semiconductor is less than 1 $g/m^2$, the decomposing effect on harmful materials is not substantially expectable. On the other hand, when the content of the photoreactive semiconductor is more than 50 $g/m^2$, the reach of actinic rays and the degree of contact with harmful materials are not increased as much. On the contrary, such a content undesirably causes leakage and dispersion of the photoreactive semiconductor because the photoreactive semiconductor cannot be firmly kept in the matrix of the photoreactive agent for removing harmful materials.

The larger the absolute amount of the photoreactive semiconductor becomes, the larger the decomposing effect on harmful materials tends to be expectable. Therefore, it is preferable to increase the content of the photoreactive semiconductor in a range where characteristics such as handling properties are satisfactory.

The organic fine particles coated with inorganic fine particles have a form in which the surfaces of organic fine particles are coated with inorganic fine particles. Also after the formation of a coating film, they have an archipelago structure in which the inorganic fine particle component is dispersed as micro particles in a matrix formed by the organic fine particle component.

When the photoreactive semiconductor is formed into a layer together with the organic fine particles coated with the inorganic fine particles, the inorganic fine particle component is located between the photoreactive semiconductor and the organic fine particle component, so that the organic fine particle component can markedly avoid the strong influence of oxidative decomposition by the photoreactive semiconductor.

As the inorganic fine particles, those which interact with the photoreactive semiconductor are used, so that the photoreactive semiconductor is preferentially located on the inorganic fine particles not only physically but also chemically. Therefore, the influence of the photoreactive semiconductor can be further suppressed.

On the other hand, in a coating film formed of a mere mixture of the photoreactive semiconductor, inorganic fine particles and organic fine particles, or a coating film formed of a mixture prepared by mixing inorganic fine particles and organic fine particles and then mixing the photoreactive semiconductor therewith, the contact of the photoreactive semiconductor with the organic fine particles is remarkably increased even when the inorganic fine particles are those which interact with the photoreactive semiconductor. Therefore, such coating films are much more liable to be influenced by the strong oxidative decomposition due to the photoreactive semiconductor than the coating film composed of the above-mentioned organic fine particles coated with inorganic fine particles and the photoreactive semiconductor.

As the inorganic fine particle component of the organic fine particles coated with inorganic fine particles according to the present invention, there may be exemplified smectites such as saponite, iron saponite, hectorite, sauconite, Stevensite, montmorillonite, Beidellite, etc.; micas such as vermiculite, phlogopite, sodium mica, Leacite mica, etc.; chlorites such as Clinochlore, chamosite, Sudoite, clintonite, margarite, Surite, etc.; kaolinites such as chrysotile, antigorite, kaolinite, dickite, nacrite, halloysite (7 Å, 10Å), etc.; and other minerals and composites, such as sepiolite, palygorskite, Fraipontite, sericite, Zeeklite®, diatomaceous earth, hydrotalcite, talc, etc.; aluminum oxides such as hydrated aluminum oxide (alumina), zeolite, etc.; aluminum hydroxide; aluminum oxidesilicon oxide composites including activated clay, acid clay, aluminum silicate, etc.; hydrated silicon oxide (silica); metal-silicic acid composites such as calcium silicate, magnesium silicate, titanium silicate, etc.; and water-insoluble or difficultly water-soluble metal oxides, hydroxides, carbonates, phosphates or sulfates, such as magnesium oxide, magnesium hydroxide, magnesium carbonate, calcium phosphate, calcium carbonate, calcium oxide, barium sulfate, zirconium oxide (zirconia), zirconium carbonate, antimony oxide, iron oxide, tin oxide, zinc oxide, titanium oxide (rutile, anatase), etc.

Of these, preferable are the water-insoluble or difficultly water-soluble metal oxides including their hydrates, such as hydrated aluminum oxide, aluminum oxide, hydrated silicon oxide, magnesium oxide, calcium oxide, zirconium oxide, antimony oxide, iron oxide, tin oxide, zinc oxide, titanium oxide, etc.; and the composite metal oxides. Particularly preferable are silicon oxide, aluminum oxide, magnesium oxide, zirconium oxide, zinc oxide and titanium oxide.

Particles of these metal oxides are prepared by various methods such as oxidation by metal combustion, dehydrating oxidation of a metal hydroxide, hydrolytic oxidation of a metal salt, and hydrolysis or oxidation by combustion of a metal alkoxide. There is also known the sol-gel process which comprises using a solution of an organic or inorganic metal compound as a starting material, hydrolyzing and polymerizing the compound in the solution to convert the solution to a sol containing metal oxide or hydroxide fine particles dissolved therein, accelerating the reaction to convert the sol to a gel, and heating the gel to prepare a solid of oxide. This process is preferable because it permits granulation at a relatively low temperature and the (hydrated) metal oxide obtained thereby is often porous.

The average particle size of inorganic fine particle component of the organic fine particles coated with inorganic fine particles according to the present invention is preferably approximately 1–60 nm, more preferably 2–40 nm. With a decrease of the particle size of the organic fine particle component, the stability of a dispersion of, at least, the organic fine particles coated with inorganic fine particles is deteriorated or the strength of a coating film formed is deteriorated. By contrast, with an increase of the particle size of the organic fine particle component, at least the photoreactive semiconductor is undesirably localized when a coating film is formed.

On the other hand, one or more components (monomers) used for preparing the organic fine particle component of the organic fine particles coated with inorganic fine particles according to the present invention and an atomization method employed for preparing the organic fine particle component are not limited so long as the organic fine particle component is insoluble and dispersible in water or a mixed medium of water as a main dispersion medium and an organic solvent while retaining a composite form without releasing the above-mentioned inorganic fine particles from their surfaces, and the organic fine particle component has by itself an ability to form a self-coating film, at least thermally.

As the monomer(s) which constitutes the organic fine particles used in the present invention, there may be exemplified olefins such as ethylene, chloroethylene (vinyl chloride), dichloroethylene (vinylidene chloride), propylene, 2-methylpentene, etc.; dienes such as 1,2-butadiene, 1,3-butadiene, isoprene, etc.; aromatic vinyl compounds such as styrene, methylstyrene, dimethylstyrene, trimethylstyrene, ethylstyrene, isopropylstyrene, butylstyrene, chloromethylstyrene, methoxystyrene, butoxystyrene, acetoxystyrene, chlorostyrene, dichlorostyrene, bromostyrene, vinyltoluene, vinylpyridine, etc.; (meth)acrylic acid esters such as methyl (meth)acrylate, ethyl (meth)acrylate, propyl (meth)acrylate, isopropyl (meth)acrylate, butyl (meth)acrylate, isobutyl (meth) acrylate, hexyl (meth)acrylate, octyl (meth)acrylate, 2-ethylhexyl (meth)acrylate, dodecyl (meth)acrylate, cyclohexyl (meth)acrylate, furfuryl (meth)acrylate, tetrahydrofurfuryl (meth)acrylate, 2-hydroxyethyl (meth)acrylate, 2-hydroxypropyl (meth)acrylate, 2-methoxyethyl (meth) acrylate, 2-butoxyethyl (meth)acrylate, 2-(2-methoxyethoxy)ethyl (meth)acrylate, phenyl (meth) acrylate, benzyl (meth)acrylate, 2-dimethylaminoethyl (meth)acrylate, 2-diethylaminoethyl (meth)acrylate, 2,2,3,3-tetrafluoropropyl (meth)acrylate, vinyl (meth)acrylate, allyl (meth)acrylate, glycidyl (meth)acrylate, etc.; crotonic acid esters such as methyl crotonate, ethyl crotonate, isopropyl crotonate, butyl crotonate, isobutyl crotonate, sec-butyl crotonate, tert-butyl crotonate, p-cresyl crotonate, vinyl crotonate, etc.; vinyl esters such as vinyl acetate, vinyl propionate, vinyl butyrate, vinyl benzoate, etc.; unsaturated fatty acid diesters such as dimethyl maleate, diethyl maleate, dibutyl maleate, di(2-ethylhexyl) maleate, dioctyl maleate, dimethyl fumarate, diethyl fumarate, dibutyl fumarate, di(2-ethylhexyl) fumarate, dioctyl fumarate, dimethyl itaconate, diethyl itaconate, dibutyl itaconate, di(2-ethylhexyl) itaconate, dioctyl itaconate, etc.; (meth)acrylamides such as acrylamide, cyclohexylacrylamide, phenylacrylamide, methyl(meth)acrylamide, ethyl(meth)acrylamide, butyl (meth)acrylamide, tert-butyl(meth)acrylamide, 2-methoxyethyl(meth)acrylamide, dimethyl(meth) acrylamide, diethyl(meth)acrylamide, etc.; and vinyl ethers such as methyl vinyl ether, butyl vinyl ether, hexyl vinyl ether, methoxyethyl vinyl ether, dimethylaminoethyl vinyl ether, etc.

The polymer obtained from any of these monomers may be either a homopolymer or a copolymer. In addition to the above-exemplified monomers, there may be copolymerized any of unsaturated fatty acids such as (meth)acrylic acid, crotonic acid, etc.; aliphatic unsaturated dibasic acid monoesters such as mono-methyl maleate, monoethyl maleate, monobutyl maleate, monomethyl itaconate, monoethyl itaconate, monobutyl itaconate, etc.; acrylonitriles; and methacrylonitriles.

Specific examples of the copolymer are styrene/butadiene copolymers, ethylene/vinyl acetate copolymers, vinyl chloride/vinyl acetate copolymers, ethylene/vinyl acetate/ vinyl chloride copolymers, styrene/maleic anhydride copolymers, styrene/maleic acid monoalkyl ester copolymers, methacrylic acid/methacrylate copolymers, styrene/methacrylic acid/methacrylate copolymers, acrylic acid/methacrylate copolymers, styrene/acrylic acid/ methacrylate copolymers, vinyl benzoate/crotonic acid copolymers, and vinyl acetate/crotonic acid/methacrylate copolymers.

There may also be exemplified copolymers in which backbone chain is a polyester, nylon or fluorocarbon polymer, and the side chain is an acrylic copolymer, styrene-based copolymer or a side chain containing a reactive atomic group such as vinyl group.

In addition, there may be used polyester resins, polycarbonate resins, polyacrylate resins, phenoxy resins, phenolic resins, butyral resins, etc.

The minimum film-forming temperature of the organic fine particles is preferably 150° C. or lower, more preferably 120° C. or lower. The film properties of the organic fine particles are, of course, preferably good. The term "film properties" used here mainly means film strength. Needless to say, the film properties have to be such that the film is free from stickiness and blocking. In the present invention, it is not preferable that pores formed by groups of particles are thermally deformed to be completely lost before film formation, so that a uniform film is formed. The reason is that when there is formed a layer containing the photoreactive semiconductor and the organic fine particles coated with inorganic fine particles, the organic fine particle component is very likely to envelop the photoreactive semiconductor and the inorganic fine particles. Therefore, ideal organic fine particles in the present invention are those which are not thermally deformed to a great degree and give a high film strength by limited contact of the particles with one another.

Although depending on the particle size of the coating organic fine particle component, the average particle size of the organic fine particle component of the organic fine particles coated with inorganic fine particles according to the present invention is preferably approximately 5–1,000 nm, more preferably 20–500 nm. With a decrease of the particle size of the organic fine particle component, the stability of a dispersion of at least the organic fine particles coated with inorganic fine particles is deteriorated, or the strength of a film formed is deteriorated. By contrast, with an increase of the particle size of the organic fine particle component, at least the photoreactive semiconductor is localyzed during film formation. Therefore, it is not preferable that the particle size of the organic fine particle component is outside the above range.

The average particle size of the organic fine particles coated with inorganic fine particles is preferably approximately 7–1,100 nm, more preferably 23–560 nm. The ratio of the particle size of the inorganic fine particle component to that of the organic fine particle component is preferably approximately 1:3 to 1:100, more preferably approximately 1:5 to 1:50. When the ratio of the particle size of the inorganic fine particle component to that of the organic fine particle component is increased, pores obtained after film formation are small, resulting in decreased contact of harmful materials with the photoreactive semiconductor. When the ratio is decreased, the film strength is deteriorated. Therefore, it is not preferable that the ratio is outside the above range.

The percentage of coverage of the organic fine particle component with the inorganic fine particle component in the organic fine particles coated with inorganic fine particles is preferably 1 to 100%, more preferably 5 to 80% when as percentage of coverage of 100%, there is taken the percentage in the case where the inorganic fine particle component is in contact with the surface of the organic fine particle component without a space for further contact of the inorganic fine particle component and without piling of inorganic fine particles. When the percentage of coverage with the inorganic fine particle component is too low, namely, the percentage of exposure of the organic fine particle component is high, the organic fine particle component tends to be deteriorated by the photoreactive semiconductor. By contrast, when the percentage of coverage with the inorganic fine particle component is too high, the fusion of organic fine particles together with one another is inhibited, resulting in a deteriorated film strength. Therefore, it is not preferable that the percentage of coverage is outside the above range. The content of the inorganic fine particle component in the organic fine particles coated with inorganic fine particles is approximately 2–80% though it cannot be unequivocally determined because it depends on the specific gravities of the organic fine particle component and the inorganic fine particle component.

The organic fine particles coated with inorganic fine particles according to the present invention may be formed, for example, by a method of forming inorganic fine particles simultaneously with the formation of organic fine particles; a method of forming organic fine particles at first, reacting an inorganic-organic interaction accelerator capable of interacting with inorganic fine particles, with the organic fine particles in the course of or after the formation of the organic fine particles, and then reacting therewith inorganic fine particles; or a method of forming at first organic fine particles so that an agent for forming inorganic fine particles may be located on the surfaces of the organic fine particles, and then forming inorganic fine particles from the agent for forming inorganic fine particles.

When granulation for preparing the inorganic fine particle component is carried out at the time of preparing the organic fine particles coated with inorganic fine particles, the above-mentioned sol-gel process may be preferentially employed.

As an example of process for producing the organic fine particles coated with inorganic fine particles according to the present invention, in the manner described above, there is a process which, as disclosed in Japanese Patent Laid-Open Nos. 59-71316 and 60-127371, comprises mixing a copolymerizable monomer with an inorganic-organic interaction accelerator (e.g. a monomer having in the molecule a polymerizable unsaturated double bond and an alkoxysilane group, or vinylsilane) and the inorganic fine particle component, and fixing the inorganic fine particle component on the surface of the organic fine particle component in the course of preparing the organic fine particle component by emulsion polymerization and granulation.

There may also be exemplified a process which comprises precipitating a silica component as inorganic fine particles on the surfaces of previously formed organic fine particles by the use of a hydrolyzable alkoxysilane non-miscible with water, such as ethyl orthosilicate, and fixing the same, as described in "Collection of summaries in international forum about polymer microspheres", pp. 181–184 (1991).

Specific examples of the inorganic-organic interaction accelerator are various coupling agents including silane coupling agents such as vinyltrichlorosilane, vinyltrimethoxysilane, vinyltriethoxysilane, tris(2-methoxyethoxy)vinylsilane, γ-glycidoxypropyltrimethoxysilane, γ-methacryloxypropyltrimethoxysilane, γ-(2-aminomethyl)aminopropyltrimethoxysilane, γ-chloropropyltrimethoxysilane, γ-mercaptopropyltrimethoxysilane, γ-aminopropyltriethoxysilane, etc.; titanate type coupling agents such as isopropyltriisostearoyl titanate, isopropyltricumylphenyl titanate, isopropyltri-n-dodecylbenzenesulfonyl titanate, isopropyltris(dioctyl pyrophosphate) titanate, tetraisopropylbis(ditridecyl phosphite) titanate, bis(dioctyl pyrophosphate)oxyacetate titanate, isopropyldimethacryloylisostearoyl titanate, etc.; aluminum-containing coupling agents such as (alkyl acetoacetate)aluminum diisopropylate; and zircoaluminate type coupling agents.

The content of the organic fine particles coated with inorganic fine particles in the layer containing at least the photoreactive semiconductor and the organic fine particles coated with inorganic fine particles may be a minimum amount at which the photoreactive semiconductor is not leaked out and dispersed from the photoreactive agent for removing harmful materials. That is, the content may be such that the layer containing at least the photoreactive semiconductor and the organic fine particles coated with inorganic fine particles forms a coating film and retains the practical film strength over a long period of time. Making the content of the organic fine particles coated with inorganic fine particles higher than such a content is not preferable because it improves the stability of the photoreactive agent for removing harmful materials but deteriorates the more important ability to remove harmful materials.

The mixing ratio of the organic fine particles coated with inorganic fine particles to the photoreactive semiconductor is preferably approximately 10:1 to 1:5 by weight, more preferably 5:1 to 1:3 by weight. It is preferable to increase the percentage of coverage of the organic fine particle component with the inorganic fine particle component in the organic fine particles coated with inorganic fine particles and increase the content of the photoreactive semiconductor in the mixture, so long as the strength of a coating film obtained from a dispersion of the mixture can be assured.

A small amount of a binder capable of forming a self-coating film may be co-used in the layer containing at least the photoreactive semiconductor and the organic fine particles coated with inorganic fine particles. The binder is preferably one which is soluble or stably dispersible together with at least the photoreactive semiconductor in water or a mixture of water and a solvent miscible with water, and forms a coating film on solvent removal and optional heating.

As the binder, there may be exemplified organic binders such as the above-mentioned organic fine particle component of the organic fine particles coated with inorganic fine particles, starches, natural gums, chitosan, alginic acid salts, cellulose derivatives (e.g. carboxymethyl cellulose and hydroxyethyl cellulose), poly(vinyl acetate)s, poly(vinyl alcohol)s, various synthetic acid emulsions, various latices of NBR, SBR, etc., poly(vinyl butyral) resins, polyurethane-ureas obtained from a polyvalent isocyanate and a polyvalent amine or a polyhydric alcohol, and aminoplast resins obtained by polymerization of an amino compound (e.g. a melamine/formaldehyde resin) and formaldehyde; and inorganic binders such as the film-forming inorganic fine particles described hereinafter.

The organic binders are superior to the inorganic binders in binding strength when used in the same amount as that of the inorganic amount, but they are very likely to be deteriorated by the photocatalytic action of the photoreactive semiconductor. Therefore, the inorganic binders are preferentially co-used. Moreover, the inorganic binders are preferable because basically, particles thereof are not thermally deformed during film formation, so that pores are formed among the particles.

The above-mentioned layer containing at least the photoreactive semiconductor and the organic fine particles coated with inorganic fine particles may be composed of either a single layer containing a mixture of at least the photoreactive semiconductor and the organic fine particles coated with inorganic fine particles, or a laminate of two separate layers, i.e., a layer containing at least the photoreactive semiconductor and a layer containing at least the organic fine particles coated with inorganic fine particles. In the photoreactive agent for removing harmful materials which has the layer containing at least the photoreactive semiconductor and the layer containing at least the organic fine particles coated with inorganic fine particles, the contact of the photoreactive semiconductor with the organic fine particle component of the organic fine particles coated with inorganic fine particles can be further avoided.

Unlike the single layer of the mixture with the photoreactive semiconductor, the separately laminated layer containing the organic fine particles coated with inorganic fine particles need not hold the photoreactive semiconductor therein, and it is sufficient that the organic fine particles coated with inorganic fine particles in this layer merely form a coating film. Therefore, the using amount of the organic fine particles coated with inorganic fine particles may be smaller than in the single layer of the mixture and is preferably 0.5 to 20 g/m$^2$, more preferably 1 to 10 g/m$^2$ irrespective of, for example, the content of the photoreactive semiconductor in the layer containing the photoreactive semiconductor.

The laminating of the separate layers makes it possible to increase the amount of the photoreactive semiconductor without greatly deteriorating the film strength, and can improve the ability to remove harmful materials by light.

In the laminating of the layer containing at least the organic fine particles coated with inorganic fine particles on the layer containing at least the photoreactive semiconductor, when it is difficult to form the layer containing the photoreactive semiconductor by using the photoreactive semiconductor alone, a binder capable of forming a self-coating film may be co-used in this layer. In this case, since the binder comes into direct contact with the photoreactive semiconductor, the binder is likely to be oxidized by the photoreactive semiconductor, or the contact of harmful materials with the photoreactive semiconductor is likely to be inhibited. Therefore, as the binder, a non-oxidizable inorganic binder capable of forming a porous film is preferable.

A layer containing a water repellent may be formed on the surface of uppermost layer of the above-mentioned photoreactive agent for removing harmful materials which comprises a substrate and a layer containing at least a photoreactive semiconductor and organic fine particles coated with inorganic fine particles which layers are formed on at least one side of the substrate, or the above-mentioned photoreactive agent for removing harmful materials which comprises a substrate, a layer containing at least a photoreactive semiconductor and a layer containing at least organic fine particles coated with inorganic fine particles which layers are formed on at least one side of the substrate, namely, the surface of the layer containing at least the organic fine particles coated with inorganic fine particles and optionally the photoreactive semiconductor.

The water repellent referred to herein is not always required to be capable of forming a coating film at least by itself, and it may be such that when water adheres to the surface of the layer containing the water repellent, water may be penetrate into other directions in at least a gaseous state. However, the surface of a coating film formed by the water repellent have to be water-repellent.

In the present invention, when the contact angle (water, 20° C.) of a layer containing only an agent capable of imparting water repellency is 90° or more, the layer is considered water-repellent, and the agent capable of giving the water-repellent surface is called a water repellent. The water repellent used in the present invention is preferably one which has a contact angle of 100° or more, and preferably one which has a contact angle of 110° or more.

As the water repellent, there may be exemplified fluorine-containing water repellents, silicone type water repellents, wax emulsion type water repellents, water repellents obtained by simultaneous use of an acrylic resin and paraffin wax, melamine type water repellents, methylolamide type water repellents, metal complex salt type water repellents, and alkylurea type water repellents. These water repellents include solvent-soluble type ones, water-dispersible type (emulsifiable type) ones, and reaction initiator (catalyst) co-use polymerization type (two-solution mixed type) ones, and any of them may be used. Of these a water repellents, the fluorine-containing water repellents and the silicone type water repellents are preferable from the viewpoint of ease of imparting water repellency, the water repellency, their weather resistance, etc.

As the fluorine-containing water repellents, there may be used fluorine-containing compounds generally used as water and oil repellents. Specific examples of the fluorine-containing compounds are perfluoro aliphatic compounds such as polytetrafluoroethylenes, tetrafluoroethylene-hexafluoropropylene copolymers, etc.; polyperfluoroalkyl acrylates or methacrylates such as polypentadecafluorooctyl (meth)acrylates, polytrifluoroethyl (meth)acrylates, etc.; perfluorourethane resins obtained by the reaction of a polyfluoroalcohol such as pentadecafluorooctanol or pentadecafluorodecanol with a polyisocyanate such as hexamethylene diisocyanate or toluene diisocyanate; and the compounds obtained by random copolymerization of terephthalic acid, a saturated polybasic acid, a saturated polyhydric alcohol and a reaction product of a polyfluoroalcohol with a polyisocyanate, which are disclosed in Japanese Patent Laid-Open No. 62-205181.

As the silicone type water repellents, there may be used silicone type compounds generally used as water repellents, softeners, mold release agents or lubricants. As the silicone type compounds, there may be exemplified dimethyl polysiloxanes, methylhydrogen polysiloxanes, methylphenyl polysiloxanes, dimethylsiloxane-methylphenylsiloxane copolymers, block copolymers of a dimethylsiloxane or a methylphenylsiloxane and a monomer other than silicones, polysiloxane compounds obtained by modifying a dimethyl polysiloxane by introducing one or more amino groups, epoxy groups, hydroxyl groups, polyether groups or the like into the end of the molecule or the side chains, and alkyl (meth)acrylate (partially) substituted derivatives obtained by substitution of the alkyl group by a dimethyl polysiloxane or a methylphenyl polysiloxane.

The water repellents including above-exemplified fluorine-containing water repellents and silicone type water repellents may be used singly or as a mixture or laminate thereof. The water repellents are used in the form of an emulsion in water or a solution in a solvent.

In addition to the water repellent and the solvent (dispersion medium), inorganic or organic binders, surfactants, crosslinking agents, antistatic agents, softeners, hardening and finishing agents, coloring agents, etc. may be incorporated into the layer containing the water repellent.

The water resistance required of the photoreactive agent for removing harmful materials of the present invention is such that in both of the following cases, even if water penetrates into the layer containing at least the photoreactive semiconductor, the penetration does not cause a gradual decrease of the film strength and hence peeling of the layer: when dirt on the surface of said removing agent is removed with a wet cloth or the like, namely, when the surface is rubbed while being brought into contact with water even for a short period of time; and when said removing agent is used under conditions of high temperature and humidity for a long period of time, namely, when the removing agent is in contact with water vapor for a long period of time though its surface is not rubbed.

The resistance of the laminate to rubbing with a dirt-removing means such as a cloth cannot be measured according to the same criterion as in the case of the resistance of the laminate to water penetration. Even if the amount of the water repellent is increased, at least the water repellency (the contact angle of water) has a definite upper limit. On the other hand, even if the mechanical film thickness can be improved by the use of the water repellent, the film strength does not reach the upper limit at all at a minimum amount of the water repellent which gives the upper limit value of the water repellency. Therefore, in the present invention, the amount of the water repellent used may be set for its minimum amount at which the contact angle of water reaches the upper limit.

Although the upper limit value of the contact angle varies depending on the kind of the water repellent, the amount of the water repellent which gives this upper limit value is substantially constant regardless of the kind of the water repellent. Although the amount of the water repellent used in the present invention is varied depending on whether the uppermost layer of the photoreactive agent for removing harmful materials of the present invention contains a photoreactive semiconductor, the amount is preferably 0.02 to 10 g/m$^2$ in general and the most suitable amount is 0.1 to 2 g/m$^2$.

As in the above-mentioned photoreactive agent for removing harmful materials of the present invention which has the uppermost layer containing a water repellent, water resistance due to a water-repellent surface can be attained also in a photoreactive agent for removing harmful materials which comprises a substrate, a layer containing at least a photoreactive semiconductor and a layer containing at least film-forming inorganic fine particles and a water repellent which layers are formed in that order on at least one side of the substrate.

That is, the film-forming inorganic fine particles can form a film because of their film-forming properties, and the same effect as that of the above-mentioned organic fine particles coated with inorganic fine particles can be brought about by the film-forming inorganic fine particles. Pores are formed in the layer containing the film-forming inorganic fine particles because of the fineness of these particles, so that the layer has at least gas permeability.

The film-forming inorganic fine particles used in the present invention are water-insoluble inorganic fine particles which are stably or almost stably dispersible in a solvent composed mainly of water and are at least capable of forming a film. The term "film-forming" used herein means that when the inorganic fine particles used in the present invention are dispersed in a suitable dispersion medium, applied on the substrate used in the present invention or the like and then dried, the resulting film is not peeled off and retain continuity even when a considerable external force is applied thereto. Therefore, if the film is cracked or returns to a powdery state owing to drying for a long period of time and mere light touch of a finger or the like to the surface of the formed film transfers a considerable amount of a powdery material, it is judged in the present invention that the inorganic fine particles have no film-forming properties.

As the film-forming inorganic fine particles used in the present invention, there may be exemplified fine particles of natural clays and minerals such as smectites (e.g. saponite, iron saponite, hectorite and montmorillonite), vermiculites, kaolinites-serpentines [e.g. kaolinite and halloysite (10)], sepiolite, etc.; colloidal silica; colloidal alumina; modified products thereof; and synthetic inorganic high-molecular weight compounds.

In the present specification, the term "modified" in the aforesaid modified products means the development of characteristics inherent in the original minerals or the impartment of other characteristics to the original minerals, which is carried out, for example, by following method: impurities or a specific atomic group is removed from the natural minerals; a desired element in elements constituting the natural minerals is replaced by another element by treatment according to a suitable method; or physical properties of the mineral surface are modified by chemical treatment with another compound. Specific examples of the modified products referred to herein are Na-montmorillonite obtained by ion exchange carried out by treating Ca-montmorillonite with sodium carbonate or the like in the presence of water, and modified products obtained by treatment with, for example, a cationic surfactant and/or a nonionic surfactant.

The synthetic inorganic high-molecular weight compounds refer to compounds which are obtained by synthesis so as to have the same composition as that of a natural mineral or by replacing one or more element of the same composition as that of a natural mineral to give characteristics equal or superior to that of the natural mineral, and are obtained by reacting two or more compounds with each other. As the synthetic inorganic high-molecular weight compounds, there may be exemplified so-called fluoro-mica having an elemental composition obtained by replacing the hydroxyl group of the structure of natural mica by fluorine, and synthetic smectite.

Specific examples of fluoro-mica are fluorophlogopite $[KMg_3(AlSi_3O_{10})F_2]$, fluoro-mica tetrasilicide $[KMg_{2.5}(Si_4O_{10})F_2]$ and Taeniolite $[KMg_2Li(Si_4O_{10})F_2]$.

The film-forming inorganic fine particles are preferably those which are in colloidal state in at least a coating fluid. Therefore, particularly when a natural material is used as the film-forming inorganic fine particles, it is necessary to grind the natural material into fine particles and remove noncolloidal substances previously by a suitable method. When the viscosity of a coating fluid prepared from the film-forming inorganic fine particles is very high, a dispersant (a viscosity depressant) such as a hexametaphosphate may be co-used. Of such film-forming inorganic fine particles, examples of film-forming inorganic fine particles preferably used in the present invention are colloidal alumina and colloidal silica which are excellent not only in ease of fluid preparation (i.e. dispersibility in preparing a dispersion of the film-forming inorganic fine particles) and characteristics of a coating fluid (e.g. coating properties) but also in film strength such as the mechanical strength and weather resistance of the film.

Colloidal alumina is amorphous or pseudoboehmite (including boehmite in wide sense)-like alumina hydrate in a colloidal state dispersed in a form of feather, fiber or disc.

As commercially available colloidal alumina, there may be exemplified Aluminasol-10, Aluminasol-20, Aluminaclearsol, Aluminasol-SH5, Aluminasol-CSA55, Aluminasol-SV102, Aluminasol-SB52 manufactured by Kawaken Fine Chemical K.K.; Cataloid-AS (AS-1, AS-2 and AS-3) and Cataloid-AP manufactured by Shokubai Kasei Kogyo K.K.; and Aluminasol-100, Aluminasol-200 and Aluminasol-520 manufactured by Nissan Kagaku Kogyo K.K.

Colloidal silica is noncrystalline silicon dioxide in a colloidal state having a particle size of approximately 4–100 nm. In general, colloidal silica refers to silicon oxide suspended in water as a hydrate though it exists also in the form of a non-aqueous suspension or fine powder. As to a production process, colloidal silica is obtained by adding a silicon tetrahalide to water or removing ions such as alkali ions while gradually neutralizing an aqueous alkali silicate solution. Such colloidal silica includes not only unmodified colloidal silca conventionally generally used but also modified colloidal silica possessing changed ionicity of particles and changed behavior thereof toward pH change which is obtained by modifying the silca surface with ions of ammonia, calcium, magnesium, alumina or the like or a compound thereof.

As commercially available colloidal silica, there may be exemplified Adelite AT-20, Adelite AT-20N, Adelite AT-30A, Adelite AT-20Q, etc. manufactured by Asahi Denka Co., Ltd.; Cataloid SA, Cataloid SN, Cataloid S-30L, Cataloid SI-30, Cataloid SI-50, Cataloid SI-350, Cataloid SI-45P, etc. manufactured by Shokubai Kasei Kogyo K.K.; Ludox LS, Ludox HS-30, Ludox SM-30, Ludox AS, Ludox AM, etc. manufactured by E.I. du Pont de Nemours & Co.; Snowtex-20, Snowtex-N, Snowtex-O, Snowtex-S, Snowtex-SS, Snowtex-20L, Snowtex-XL, Snowtex-AK, Snowtex-UP, etc. manufactured by Nissan Kagaku Kogyo K.K.; and Silicadol-20, Silicadol-20A, Silicadol-20P, etc. manufactured by Nihon Kagaku Kogyo K.K.

The amount of the film-forming inorganic fine particles in the layer containing at least the film-forming inorganic fine particles and a water repellent according to the present invention is preferably 1 to 100 g/m$^2$.

In general, with an increase of the amount of the film-forming inorganic fine particles, the powder-dropping properties of the photoreactive semiconductor in the layer under the film-forming inorganic fine particles is improved but the ability to remove harmful materials by light is deteriorated. When the amount of the film-forming inorganic fine particles is less than 1 g/m$^2$, the powder-dropping properties are substantially the same as that before coating with the film-forming inorganic fine particles. To improve the powder-dropping properties, an amount of the film-forming inorganic fine particles of 100 g/m$^2$ is sufficient. A larger amount of the film-forming inorganic fine particles merely deteriorates the ability to remove harmful materials by light and hence is not preferable. The amount of the film-forming inorganic fine particles are more preferably 2 to 50 g/m$^2$, most preferably 5 to 40 g/m$^2$.

As the water repellent used in the layer containing at least the film-forming inorganic fine particles and the water repellent, all of the above-exemplified ones may be used. On the other hand, although the amount of the water repellent is varied depending on the amount of the film-forming inorganic fine particles mixed and the kind thereof, it is preferably 0.05 to 10 g/m$^2$ in general and the most suitable amount is 0.2 to 3 g/m$^2$.

To form the layer containing at least the film-forming inorganic fine particles and the water repellent, it is sufficient that the layer containing at least a photoreactive semiconductor is coated or impregnated with a coating fluid containing at least the film-forming inorganic fine particles and the water repellent. It is preferable that the coating or impregnation has no undesirable influence such as dissolution on the layer containing at least a photoreactive semiconductor and that the layer formation is carried out at as low a solid content of the coating fluid as possible so long as the coating conditions such as drying are satisfied.

The above-mentioned layer containing at least film-forming inorganic fine particles and a water repellent may be a laminate of two separate layers, i.e., a layer containing at least film-forming inorganic fine particles and a layer containing at least a water repellent. In this case, the water repellent can be localized on the surface of the photoreactive agent for removing harmful materials, so that more effective exhibition of the water resistance is possible.

Also in the case of the laminate of the layer containing at least film-forming inorganic fine particles and the layer containing at least a water repellent, there may be used the same film-forming inorganic fine particles and water repellent as used for forming the above-mentioned layer containing at least film-forming inorganic fine particles and a water repellent.

In the case of the laminate of the layer containing at least film-forming inorganic fine particles and the layer containing at least a water repellent, the content of the film-forming inorganic fine particles may be the same as in the above-mentioned mixed layer of film-forming inorganic fine particles and a water repellent from the viewpoint of the film strength and is preferably 1 to 100 g/m$^2$. In the layer containing a water repellent, the content of the water repellent is preferably 0.05 to 8 g/m$^2$ and the most suitable content is 0.2 to 2 g/m$^2$.

In the above-mentioned photoreactive agent for removing harmful materials, a layer containing at least film-forming inorganic fine particles may be formed between the substrate and the layer containing at least a photoreactive semiconductor because this formation can prevent the deterioration of the substrate by the photoreactive semiconductor over a long period of time even when the substrate is oxidizable. In this layer containing at least film-forming inorganic fine particles, the same film-forming inorganic fine particles as above may be used.

In this layer containing film-forming inorganic fine particles, there may be used, together with the film-forming inorganic fine particles, clay, kaolin, talc, calcium carbonate, sericite, barium sulfate, alumina, silica, magnesium carbonate, aluminum hydroxide, titanium oxide having no photocatalytic capability, and inorganic pigments having no film-forming properties, such as zinc oxide.

The thickness of the layer containing at least film-forming inorganic fine particles which is formed between the substrate and the layer containing at least a photoreactive semiconductor may be such that at least the oxidative effect of the photoreactive semiconductor is not exercised on the substrate and that a continuous coating film can be formed. The thickness is preferably 0.5 μm or more, more preferably 2 to 10 μm.

In the layer containing at least a photoreactive semiconductor, a carrier may be co-used in addition to organic fine particles coated with inorganic fine particles, and film-forming inorganic fine particles.

In the formation of the layer containing at least a photoreactive semiconductor, when the photoreactive semiconductor is supported on the surface of a carrier to form larger granules before mixing the photoreactive semiconductor with other components which constitute said layer, the photoreactive semiconductor becomes easy to hold in a matrix composed of the other layer-forming components. Therefore, the leakage and dispersion of the photoreactive semiconductor can be prevented during the production and use and moreover the inactivation of active sites on the surface of the photoreactive semiconductor can be considerably suppressed as compared with an aggregate of the photoreactive semiconductor alone.

Specific examples of the carrier used in the present invention are silicon oxide (silica), aluminum oxide (alumina), zirconium oxide (zirconia), magnesium oxide (magnesia), aluminum hydroxide, magnesium hydroxide, zirconium hydroxide, calcium hydroxide, activated clay, zeolite, sepiolite, halloysite, hydroapatite, zinc oxide, silica-alumina composite, silica-zinc oxide composite, silica-magnesia composite, zinc oxide-magnesia composite, silica-alumina-zinc oxide composite, silica-alumina-magnesia composite, and activated carbons prepared from various materials such as wood chips and coconut husks.

When there is used a carrier having gas adsorbability in itself, such as activated clay, zeolite, sepiolite and activated carbon among the above-exemplified carriers, the ability to remove harmful materials without light irradiation is also improved. In the case of this gas adsorbability, the gas adsorption is physical adsorption and is in thermal equilibrium. Therefore, when the temperature of the carrier is raised by light irradiation, harmful materials adsorbed on the carrier without light irradiation are released and at the same time, decomposed by the photoreactive semiconductor supported on the carrier. Of such carriers having gas adsorbability, there are carriers which preferentially adsorb a specific compound or either an acidic substance or a basic substance. Therefore, it is preferable to select the most suitable carrier from the above-exemplified carriers, depending on use conditions. If necessary, the carriers are preferably used in combination.

The flame retardance of the photoreactive agent for removing harmful materials can be improved by using as the carrier a hydrated oxide capable of releasing water owing to heat, such as aluminum hydroxide, magnesium hydroxide, zirconium hydroxide, calcium hydroxide or the like.

The specific surface area of the carrier used in the present invention is preferably approximately 50–2,000 $m^2/g$. When activated carbon is used, its specific surface area is preferably approximately 500–1,500 $m^2/g$.

On the other hand, for the purpose of the present invention, the particle size of the carrier is preferably large to a certain extent, namely, at least about 10 times as large as that of the photoreactive semiconductor co-used. The preferable particle size of the carrier used in the present invention is 100 nm to 50 $\mu$m. In particular, the preferable particle size of activated carbon is 50 nm to 10 $\mu$m. The carrier may be used either in the form of granules or in the form of pellets or tablets prepared by molding the granules.

The content of the carrier in the photoreactive agent for removing harmful materials of the present invention is determined by the mixing ratio of the photoreactive semiconductor to the carrier. That is, the mixing ratio of the photoreactive semiconductor to the carrier is preferably 1:30 to 10:1, more preferably approximately 1:10 to 5:1. When the mixing ratio of the photoreactive semiconductor to the carrier is too high in the case where the absolute amount of the photoreactive semiconductor is definite, the content of the carrier in the photoreactive agent for removing harmful materials becomes too high, so that it becomes difficult to hold the photoreactive semiconductor and the carrier in the matrix of the photoreactive agent for removing harmful materials. When the mixing ratio is too low, the effect of co-use of the carrier is substantially not obtainable.

It is not necessary that the carrier should be only that supporting the photoreactive semiconductor. There may be used a carrier supporting the photoreactive semiconductor and a carrier supporting no photoreactive semiconductor, in combination or separately.

Lastly, there are explained below the substrate on which the above-mentioned layer containing at least a photoreactive semiconductor is to be formed and a method for forming the layer(s) on the substrate.

As the substrate used in the present invention, there may be exemplified paper, cloth, nonwoven fabric, wood, plywood, concrete panels, wall materials, gypsum, plastics films or boards of a poly(vinyl chloride), polyester or the like, steel plates, iron plates, aluminum plates, tin plates, glass plates, and composites and (bonded) laminates thereof.

Of these, paper composed mainly of vegetable fiber and nonwoven fabric composed mainly of synthetic resin (fiber) are preferable as the substrate used in the present invention. These substrates may be used not only in a flat form but also in a galvanized panel form or in a composite form thereof (e.g. corrugated structure or honeycomb structure).

As the vegetable fiber used as a material for the substrate used in the present invention, there may be used kraft pulps obtained from softwood or hardwood; chemical pulp such as sulfite pulp, alkali pulp, etc.; wood fibers such as semichemical pulp, semimechanical pulp, mechanical pulp, etc.; vegetable non-wood fibers such as Broussonetia kazinoki, Edgeworthia papyrifera, straw, kenaf, bamboo, linter, bagasse, esparto, etc.; regenerated fibers such as rayon, etc.; processed fibers of natural materials, such as cellulose derivative fibers, etc.

In addition, as the vegetable fiber used as a material for the substrate used in the present invention, there may be used inorganic-material-supporting fiber obtained by reacting the vegetable fiber with a water-soluble inorganic material before its formation into a sheet and then making the inorganic material water-insoluble. As to a method for supporting the water-soluble inorganic material and making the same water-insoluble, a hydrophilic fiber material is impregnated with an aqueous solution containing a water-soluble compound capable of reacting with a specific gas of aqueous solution to become water-insoluble, after which the inorganic material is brought into contact with a gas or an aqueous solution, which makes the inorganic material water-insoluble, whereby the water-insoluble inorganic material can be supported inside the fiber material.

As the synthetic resin fiber, there may be exemplified thermoplastic synthetic resin fibers of olefin resins (e.g. polyethylenes and polypropylenes), polyester type resins (e.g. Dacron), poly(vinyl acetate)s, ethylene-vinyl acetate copolymer resins, polyamide resins (e.g. nylons), polyacrylonitrile resins (e.g. Acrylan, Orlon, Dynel and Verel), poly(vinyl chloride)s, poly(vinylidene chloride)s, polystyrenes, poly(vinyl ether)s, poly(vinyl ketone)s, polyethers, poly(vinyl alcohol)s, diene type resins, polyurethane resins, etc.; thermosetting resins such as phenolic resins, furan resins, urea resins, melamine resins, aniline resins, unsaturated polyester resins, alkyd resins, epoxy resins, etc.; silicone resins; fluoro-resins; metal fiber of stainless steel, etc.; and various glass fibers. In the present example, the above-exemplified fibers may be used singly or in combination.

When the photoreactive agent for removing harmful materials of the present invention is used for removing harmful materials in a life space by its use in a wall material, ceiling material, wall paper, curtain or the like, at least the substrate used in the photoreactive agent for removing harmful materials is also preferably flame-retardant.

As fiber capable of imparting flame retardance, there may be exemplified halogen-containing fiber and aramid fiber, whose molecules themselves are flame-retardant; inorganic fibers which are intrinsically non-combustible, such as metal fiber, ceramic fiber, rock wool fiber, glass fiber, alumina fiber, zirconia fiber, silicon nitride fiber, silicon carbide fiber, carbon fiber, etc.; and fibers obtained by chemically or physically incorporating a flame retardant into generally used fiber. There may also be used a product obtained by treating a substrate made of generally used fiber with a flame retardant.

Of such substrates, those preferably used from the viewpoint of processability and material cost are substrates made of fiber obtained by chemically or physically incorporating generally used fiber with a well-known flame retardant such as any of water-soluble inorganic salts (e.g. $NH_4Br$, $NH_4VO_3$, $Na_3VO_4$, $(NH_4)_2MoO_4$ and $Na_2MoO_4.2H_2O$), phosphorus- and nitrogen-containing derivatives (ethylenimine phosphate, guanidine phosphate and phosphorylphosphoramide), the phosphorus-containing halide type flame retardants disclosed in U.S. Pat. Nos. 2,725,311 and 3,087,836, and the antimony trioxidehalogen type flame retardants disclosed in U.S. Pat. No. 3,300,426 and Japanese Patent Examined Publication No. 48-35604; and the substrates treated with a flame retardant.

Anti-flaming or antiflaming agents for organic polymers are described in detail in J. W. Lyons "The Chemistry and Uses of Fire Retardants" (John Willey) 1970. The techniques described therein may be applied.

As fiber which constitutes the nonwoven fabric used as the substrate used in the present invention, activated-carbon fiber is also suitable. The activated-carbon fiber has an adsorption rate 100 to 1,000 times as high as that of common powdery activated carbon and has an adsorption per unit amount which is about 10 times as large as that of the latter. Since the activated-carbon fiber is formed by calcining starting fiber, it is intrinsically non-combustible and hence is advantageously used also for imparting flame retardance to photoreactive agent for removing harmful materials.

In processing the above-exemplified vegetable fiber material into the substrate used in the present invention, there may be added various additives such as sizing agents (e.g. rosin, its modified products, emulsions of a maleic anhydride-based synthetic resin or a styrene/acrylate synthetic resin, alkylketene dimers, and alkenylsuccinic anhydrides), strength improvers and binders [e.g. starch, its modified products, carboxymethyl cellulose, poly(vinyl alcohol)s, poly(ethylene oxide)s, polyethylenimines, polyacrylamides, polyamidoepichlorohydrins, various emulsions (including latices), urea-formaldehyde resins and melamine-formaldehyde resins], yield improvers, surfactants, defoaming agents, dyes, fluorescent whitening agents, antioxidants, slime-controlling agents, etc.

For producing the substrate, there may be used a cylinder paper machine, Foordrinier paper machine, Yankee paper machine, twin-wire paper machine, and combination paper machines such as hybrid former top former.

The nonwoven fabric used as the substrate used in the present invention may be produced, for example, by a wet process comprising suspending the above-exemplified synthetic resin fiber in water and forming the suspension into a sheet by a paper making method; a so-called dry process such as resin bonding comprising bonding of a resin, needle punching utilizing crossing by means of a needle, stitch bonding comprising knitting out of yarn, and thermal bonding comprising bonding by heat; a water-flow entangling process comprising entangling fibers with one another by jetting high-pressure water through a nozzle; spun bonding comprising forming a sheet with direct spinning; or a melt blow process comprising forming a sheet while forming very fine fibers by applying the principle of atomization at the time of direct spinning.

Since the nonwoven fabric is subjected to aqueous treatment in the present invention, it has to possess a water-wettability to a certain extent and hence is preferably that obtained from a web prepared from hydrophilic fiber. From the viewpoint of sheet strength, the nonwoven fabric is preferably processed by spun bonding or a spun lace process.

Each of the photoreactive agents for removing harmful materials which have been explained above [i.e., the photoreactive agent for removing harmful materials which has a layer containing at least a photoreactive semiconductor and organic fine particles coated with inorganic fine particles; the photoreactive agent for removing harmful materials which has a layer containing at least a photoreactive semiconductor and a layer containing at least organic fine particles coated with inorganic fine particles which layers are formed in that order; the same photoreactive agent for removing harmful materials as above except for further having a layer containing a water repellent, on at least the above-mentioned layer containing organic fine particles coated with inorganic fine particles; the photoreactive agent for removing harmful materials which has a layer containing at least a photoreactive semiconductor and a layer containing at least film-forming inorganic fine particles and a water repellent which layers are formed in that order; the photoreactive agent for removing harmful materials which has a layer containing at least a photoreactive semiconductor, a layer containing at least film-forming inorganic fine particles, and a layer containing at least a water repellent which layers are formed in that order; the same photoreactive agent for removing harmful materials as above except for further having a layer containing at least film-forming inorganic fine particles, between a substrate and the layer containing at least a photoreactive semiconductor] comprises the above-mentioned substrate and the layer(s) formed on at least one side of the substrate, and is obtained by coating or impregnating at least one side of a previously prepared substrate with one or more aqueous dispersions containing layer-forming components including a photoreactive semiconductor, and drying the thus treated substrate.

As a method for the coating or impregnation of the substrate with a coating fluid for layer formation according to the present invention, there are exemplified a method of impregnating the substrate with the coating fluid by means of a conventional size press, a gate roll size press, a film transfer type size press or the like; a method of coating the substrate with the coating fluid and optionally a small amount of a suitable binder by the same procedure as a conventional coating procedure, by means of a coater such as a roll coater, rod (bar) coater, blade coater, spray coater, air doctor (knife) coater, curtain coater or the like. Particularly in the impregnation method, the substrate may be previously wetted.

In the coating with the coating fluid for layer formation, when the substrate surface is poor in water-wettability, it is preferable to incorporate a suitable surfactant into the coating fluid or improve the water-wettability of the substrate surface by a physical or chemical treatment such as corona treatment, glow discharge treatment, plasma treatment, electron radiation treatment, far-ultraviolet irradiation treatment, ozone treatment, treatment with a surfactant, or the like.

In the present invention, a product obtained in the following process is also regarded as a photoreactive agent for removing harmful materials which has one or more layers on at least one side of a substrate: from one or more layer-forming components and one or more substrate-forming components in a layer which comes into contact with the substrate of a photoreactive agent for removing harmful materials which is to be produced, for example, a layer containing at least a photoreactive semiconductor and organic fine particles coated with inorganic fine particles, the substrate is prepared while supporting the layer-forming component(s) such as a photoreactive semiconductor on the surface of the substrate-forming component(s).

The substrate-forming component referred to herein is a component necessary for keeping the shape of a photoreactive agent for removing harmful materials which is obtained by forming an aqueous dispersion of aggregates into a sheet. The substrate-forming component is preferably fibrous. As a material for this fiber, a thermoplastic resin is preferable from the viewpoint of substrate-forming properties and post-processability. There may be used the above-exemplified thermoplastic fibers which constitute the nonwoven fabric preferably used as the substrate used in the present invention.

As to a process for producing such a photoreactive agent for removing harmful materials, it may be produced from the substrate-forming component(s) and layer-forming component(s) by basically the same process as the above production process of the substrate.

Of the photoreactive agents for removing harmful materials of the present invention, those substantially comprising a substrate and two or more layers laminated thereon [e.g. the photoreactive agent for removing harmful materials which has a layer containing at least a photoreactive semiconductor and a layer containing at least organic fine particles coated with inorganic fine particles which are formed in that order] may be obtained by forming a lowermost layer on the substrate by the above-mentioned integral-sheet formation process, and laminating upper layer(s) thereon by coating or impregnation.

In the case of the photoreactive agents for removing harmful materials of the present invention, an undercoating layer or an intermediate layer may, if desired, be laminated in the formation of each layer in order to improve the adhesive properties, etc. When the photoreactive agent for removing harmful materials of the present invention is used by joining one side thereof to another substrate, an objective equipment or the like or feeding only one side thereof with a gas containing an objective substance to be decomposed, at least a layer containing a photoreactive semiconductor and optionally other layers may be formed only on one side of the substrate used in the present invention.

In addition, when a layer containing a photoreactive semiconductor and optionally other layers are formed on each side of the substrate, the combination of these layers and the kind and content of component(s) contained in each layer on one side may be different from those on the other side.

According to the present invention, there can be provided a photoreactive agent for removing harmful materials which utilizes the photocatalytic capability of a photoreactive semiconductor, is excellent in ability to remove harmful materials such as malodor, can hold the photoreactive semiconductor excellently, can be given water resistance and the like if necessary, and can easily be produced.

The photoreactive agent for removing harmful materials can be utilized in the following by making the most suitable its substrate, a combination of layers formed thereon and the kind and content of component(s) contained in each layer: articles in life spaces such as clothing, curtains, blinds, electric appliances, illuminators, walls, doors, ceilings, floors, table cloths, furniture, and the trims of automobiles, trains, airplanes and the like; filters of air conditioners and air cleaners; and the exteriors and surfaces of structures such as erections (e.g. houses and buildings), utility poles, signals, roads, roadside zones, bridges, etc.

DESCRIPTION OF THE PREFERRED EMBODIMENTS

The present invention is further explained in detail with the following examples, which should not be construed as limiting the scope of the invention, within the scope of the gist of the invention. In the examples, weight ratio, amount of coating, and percentage by weight are all expressed in terms of nonvolatile content (drying residue) unless otherwise specified.

EXAMPLE 1

With water were mixed 100 parts by weight of cold-dried metatitanic acid (MCH, mfd. by Isihara Sangyo Kaisha, Ltd.) as photoreactive semiconductor and 1.2 parts by weight of polycarboxylic acid ammonium salt (Microsole KE-511, mfd. Gooh Kagaku Kogyo K.K.; active ingredient 40 wt %), and dispersed with a DYNO-MILL (mfd. by WAB), a horizontal disc type mill to prepare a 20% photoreactive semiconductor dispersion A.

To 146 parts by weight of an emulsion of phenoxy resin (KE-316, mfd. by Toto Kasei K.K.; 48 wt %) as organic fine particles was added 104 parts by weight of water, and the resulting mixture was heated with stirring. When the temperature of the mixture reached 60° C., 260 parts by weight of ethyl orthosilicate (40 wt %) diluted with ethanol was slowly dropped thereinto, followed by adding thereto 104 parts by weight of water. The heating was further continued to remove the ethanol from the system, and the concentration was adjusted with water to prepare an (inorganic fine particles)-coated organic fine particles dispersion A (40 wt %) in which silica inorganic fine particles had been formed on the surfaces of phenoxy resin fine particles.

The (inorganic fine particles)-coated organic fine particles had a particle size of 0.1 $\mu$m and an inorganic fine particles content of 30 wt %.

To 60 parts by weight of the (inorganic fine particles)-coated organic fine particles dispersion A was added 10 parts by weight of water, followed by adding thereto 30 parts by weight of the photoreactive semiconductor dispersion A with stirring, whereby there was prepared a coating fluid for layer formation 1 containing the photoreactive semiconductor and the (inorganic fine particles)-coated organic fine particles

[photoreactive semiconductor:(inorganic fine articles)-coated organic fine particles=1:1 in terms of solids].

A soda-lime glass plate of 20 mm thickness as substrate was spray-coated with the coating fluid for layer formation 1 so that the amount of coating might be 50 g/m$^2$. Thus, a layer containing the photoreactive semiconductor and the (inorganic fine particles)-coated organic fine particles was formed to obtain a photoreactive agent 1 for removing harmful materials.

EXAMPLE 2

With water were mixed 100 parts by weight of zinc oxide-containing composite phyllosilicate salt (Mizukanite AP, mfd. by Mizusawa Industrial Chemicals, Ltd.; particle size about 3 μm) as carrier and 3.5 parts by weight of the same polycarboxylic acid ammonium salt (active ingredient 40 wt %) as used in Example 1, and dispersed with a DYNO-MILL as in Example 1 to prepare a carrier dispersion A having a solid content of 20 wt %.

To 50 parts by weight of the carrier dispersion A was added 50 parts by weight of the photoreactive semiconductor dispersion A prepared in Example 1, and thoroughly stirred to support the photoreactive semiconductor on the carrier surface.

To 35 parts by weight of Mowinyl 8020 manufactured by Hoechst Gosei K.K. (inorganic fine particle component: silica, organic fine particle component: acrylate copolymer resin; 43 wt %) [hereinafter referred to as (inorganic fine particles)-coated organic fine particles dispersion B], a commercially available (inorganic fine particles)-coated organic fine particles dispersion was added 5 parts by weight of water, and 60 parts by weight of the (photoreactive semiconductor)-supporting carrier dispersion prepared in the above was added with stirring, whereby there was prepared a coating fluid for layer formation 2 containing the photoreactive semiconductor, the (inorganic fine particles)-coated organic fine particles and the carrier [photoreactive semiconductor:(inorganic fine particles)-coated organic fine particles:carrier=2:5:2 in terms of solids).

The surface of an iron plate (60 cm wide, 200 mm long and 0.2 mm thick) as substrate was continuously coated with the coating fluid for layer formation 2 by means of a fountain coater so that the amount of coating might be 30 g/m$^2$. Thus, a layer containing the photoreactive semiconductor, the (inorganic fine particles)-coated organic fine particles and the carrier was formed to obtain a photoreactive agent 2 for removing harmful materials.

EXAMPLE 3

A flame-retardant sheet (80 cm wide, 300 mm long and 0.1 mm thick) (mfd. by Bandoh Kagaku K.K.) composed mainly of vinyl chloride and containing a flame retardant was used as a substrate. The sheet was continuously coated with the coating fluid for layer formation 2 prepared in Example 2, by means of a comma coater so that the amount of coating might be 20 g/m$^2$. Thus, a layer containing the photoreactive semiconductor, the (inorganic fine particles)-coated organic fine particles and the carrier was formed to obtain a photoreactive agent 3 for removing harmful materials.

EXAMPLE 4

70 Parts by weight of hardwood bleached kraft pulp and 30 parts by weight of softwood bleached kraft pulp were separately beaten to freeness (Canadian standard freeness) values of 350 ml and 400 ml, respectively. To 100 parts by weight of mixed pulp of them were added 1 part by weight of an emulsion of a 50:50 mixture of alkenylsuccinic anhydride (FIBRAN, mfd. by Ohji National K.K.) and cationized starch (Catof, mfd. by Ohji National K.K.) and 0.25 part by weight of a polyamidoepichlorohydrin (Arafix-100, mfd. by Arakawa Chemical Co., Ltd.). Using the resulting mixture, paper with a basis weight of 80 g/m$^2$ was made with a Foordrinier paper machine.

Using a dip-type impregnating apparatus, the above-mentioned base paper was passed through an aqueous fluid prepared by adding a very small amount of a surfactant [polyoxyethylene monolaurate] to an aqueous dispersion of hydroxyapatite and a styrene/acrylic emulsion (Polytron F320, mfd. by Asahi Chemical Industry Co.) in the weight ratio of 4:1, while dipping the base paper therein, so that the amount of coating might be about 3 g/m$^2$ (the total on both sides). The thus treated base paper was dried with hot air to obtain a substrate.

A sheet of the paper was continuously coated as a substrate with the coating fluid for layer formation 2 prepared in Example 2, by means of a comma coater so that the amount of coating might be 10 g/m$^2$. Thus, a layer containing a photoreactive semiconductor, (inorganic fine particles)-coated organic fine particles and a carrier was formed to obtain a photoreactive agent 4 for removing harmful materials.

EXAMPLE 5

With water were mixed 100 parts by weight of magnesium oxide (Kyowamag 30, mfd. by Kyowa Kagaku K.K.) as carrier and 3.5 parts by weight of the same polycarboxylic acid ammonium salt (active ingredient 40 wt %) as used in Example 1, and they were dispersed with a DYNO-MILL as in Example 1 to prepare a 20 wt % carrier dispersion B.

There was prepared an emulsion polymerization liquid of ethyl acrylate (EA) and 2-hydroxyethyl methacrylate (HEMA) (monomer ratio; EA/HEMA=50/1). The content of organic fine particles in the emulsion polymerization liquid was 26 wt %. Then, 500 parts by weight of the emulsion polymerization liquid was heated at 70° C. and 243 parts by weight of ethyl orthosilicate was slowly dropped thereinto, after which the heating was continued for another 6 hours to remove the ethanol from the system, and the concentration was adjusted with water to prepare an (inorganic fine particles)-coated organic fine particles dispersion C (40 wt %) in which silica inorganic fine particles had been formed on the surfaces of acrylic resin fine particles.

The (inorganic fine particles)-coated organic fine particles had a particle size of 0.08 μm and an inorganic fine particles content of 35 wt %.

To 50 parts by weight of the carrier dispersion B were added 50 parts by weight of the carrier dispersion A prepared in Example 2 and 100 parts by weight of the photoreactive semiconductor dispersion A prepared in Example 1, and the resulting mixture was thoroughly stirred to support the photoreactive semiconductor on the carrier surface.

To 200 parts by weight of the (photoreactive semiconductor)-supporting carrier dispersion were added 20 parts by weight of colloidal silica (Snowtex UP, mfd. by Nissan Kagaku K.K.; 20 wt %) as film-forming inorganic fine particles and then 60 parts by weight of the (inorganic fine particles)-coated organic fine particles dispersion C prepared in the above, and 20 parts by weight of water was added with stirring to prepare a coating fluid for layer formation 3 containing the photoreactive semiconductor, the (inorganic fine particles)-coated organic fine particles, the carrier and the film-forming inorganic fine particles [photoreactive semiconductor:(inorganic fine particles)-coated organic fine particles:carrier:film-forming inorganic fine particles=5:6:5:2 in terms of solids).

A concrete panel (90 cm wide, 180 mm long and 35 mm thick) was spray-coated as a substrate with the coating fluid for layer formation 3 so that the amount of coating might be 150 g/m$^2$. Thus, a layer containing the photoreactive semiconductor, the (inorganic fine particles)-coated organic fine particles, the carrier and the film-forming inorganic fine particles was formed to obtain a photoreactive agent 5 for removing harmful materials.

EXAMPLE 6

To water were added 60 parts by weight of poly(ethylene terephthalate) fiber with a fineness of 1.5 d and a fiber length of 15 mm (mfd. by Teijin Ltd.) and 40 parts by weight of low-melting heat-fusible fiber having a core-sheath structure [Melty #4080, mfd. by Unitica Ltd.; sheath: poly(ethylene terephthalate) copolymer, core: poly(ethylene terephthalate)] together with a small amount of a surfactant (hexaglyceryl laurate, and the resulting mixture was vigorously stirred with a pulper until bundles of fibers disappeared. The stirred mixture was diluted with water and then increased in viscosity by adding an aqueous polyacrylamide solution with mild stirring by means of an agitator. The stirring was continued to obtain a slurry of uniformly dispersed fibers.

Using the slurry, a web was prepared with a cylinder paper machine so as to have a basic weight of 80 g/m$^2$, after which it was dried with cylinder hot air of 120° C. to obtain nonwoven fabric.

The nonwoven fabric was impregnated as a support with the coating fluid for layer formation 3 so that the amount of coating might be 20 g/m$^2$. Thus, a layer containing a photoreactive semiconductor, (inorganic fine particles)-coated organic fine particles, a carrier and film-forming inorganic fine particles was formed on each side of the substrate to obtain a photoreactive agent 6 for removing harmful materials.

EXAMPLE 7

Polyester fiber with a fineness of 3 d and a fiber length of 38 mm, polyester fiber with a fineness of 6 d and a fiber length of 51 mm and viscose rayon fiber with a fineness of 3 d and a fiber length of 51 mm were splitted and mixed in the weight ratio of 5:3:2 to prepare a web. Then, the web was impregnated with a silicone/acrylic emulsion (Cylane ARJ-12L, mfd. by Nihon Junyaku K.K.), a thermoplastic binder to be given inter-fiber strength, whereby a substrate having a basic weight of 50 g/m$^2$ and a bulk density of 0.05 g/cm$^3$ was prepared.

Kunipia F (montmorillonite type swellable clay, mfd. by Kunimine Kogyo K.K.) was dispersed in water as film-forming inorganic fine particles, and the resulting dispersion and the same photoreactive semiconductor dispersion A as used in Example 1 were mixed in the ratio of 1:4 in terms of solids to prepare a coating fluid for layer formation 4 containing the photoreactive semiconductor and the film-forming inorganic fine particles.

The substrate prepared in the above was impregnated with the coating fluid for layer formation 4 so that the amount of coating might be 60 g/m$^2$ (the total on both sides). Thus, there was obtained a sheet in which a layer containing the photoreactive semiconductor and the film-forming inorganic fine particles had been formed on each side of the substrate.

The surface of this sheet was impregnated with a coating fluid for layer formation 5 containing (inorganic fine particles)-coated organic fine particles which had been prepared by adding 50 parts by weight of water to 50 parts by weight of Mowinyl 8800 mfd. by Hoechst Gosei K.K. (inorganic fine particle component: silica, organic fine particle component: acrylate copolymer resin; 40 wt %) [hereinafter referred to as "(inorganic fine particles)-coated organic fine particles dispersion D"], a commercially available (inorganic fine particles)-coated organic fine particles dispersion, so that the amount of coating might be 20 g/m$^2$ (the total on both sides). Thus, a layer containing the (inorganic fine particles)-coated organic fine particles was separately laminated on the layer containing the photoreactive semiconductor and the film-forming inorganic fine particles, to obtain a photoreactive agent 7 for removing harmful materials.

EXAMPLE 8

Into 500 parts by weight of an emulsion polymerization liquid of mixed polyester resin (Vylonal, mfd. by TYOBO Co., Ltd.) as organic fine particles was slowly dropped 485 parts by weight of ethyl orthosilicate (50 wt %) diluted with ethanol, while heating the emulsion polymerization liquid at 75° C. The heating was continued for another 6 hours to remove the ethanol from the system, and the concentration was adjusted with water to prepare an (inorganic fine particles)-coated organic fine particles dispersion E (40 wt %) in which silica inorganic fine particles had been formed on the surfaces of mixed polyester resin fine particles.

The (inorganic fine particles)-coated organic fine particles had a particle size of 0.08 μm and an inorganic fine particles content of 35 wt %.

To 50 parts by weight of the carrier dispersion A prepared in Example 2 were added 50 parts by weight of the carrier dispersion B prepared in Example 5 and 100 parts by weight of the photoreactive semiconductor dispersion A prepared in Example 1, and the resulting mixture was thoroughly stirred to support the photoreactive semiconductor on the surfaces of the carriers.

To 200 parts by weight of the resulting (photoreactive semiconductor)-supporting carriers dispersion was added 80 parts by weight of (inorganic fine particles)-coated organic fine particles dispersion E prepared in the above, and 20 parts by weight of water was added with stirring to prepare a coating fluid for layer formation 6 containing the photoreactive semiconductor, the (inorganic fine particles)-coated organic fine particles and the carriers [photoreactive semiconductor:(inorganic fine particles)-coated organic fine particles:carriers=5:8:5 in terms of solids].

An aluminum plate (50 cm wide, 60 mm long and 0.2 mm thick) was continuously coated as a substrate with the coating fluid for layer formation 6 by means of a fountain coater so that the amount of coating might be 60 g/m$^2$. Thus, a layer containing the photoreactive semiconductor, the (inorganic fine particles)-coated organic fine particles and the carriers was formed to obtain a photoreactive agent 8 for removing harmful materials.

EXAMPLE 9

The surface of a cotton woven fabric with a basic weight of 150 g/m$^2$ was continuously impregnated as a substrate with the coating fluid for layer formation 6 prepared in Example 8, with a gate roll coater so that the amount of coating might be 40 g/m² (the total on both sides). Thus, a layer containing a photoreactive semiconductor, (inorganic fine particles)-coated organic fine particles and carriers was formed to obtain a photoreactive agent 9 for removing harmful materials.

EXAMPLE 10

Colloidal alumina (Cataloid AS-3, mfd. by Shokubai Kasei Kogyo K.K.) was dispersed in water as film-forming inorganic fine particles, and the resulting dispersion and the same photoreactive semiconductor dispersion A as used in Example 1 were mixed in the ratio of 1:4 in terms of solids to prepare a coating fluid for layer formation 7 containing the photoreactive semiconductor and the film-forming inorganic fine particles.

The same substrate as used in Example 3 was coated with the coating fluid for layer formation 7 so that the amount of coating might be 30 g/m², whereby there was obtained a sheet in which a layer containing the photoreactive semiconductor and the film-forming inorganic fine particles had been formed on one side of the substrate.

On the other hand, magnesium aluminate metasilicate was dispersed in water as inorganic fine particles together with a very small amount of a surfactant (Surfinol 440, mfd. by Nissin Kagaku Kogyo K.K.), and the resulting dispersion, methyl methacrylate, butyl methacrylate, butyl acrylate and 3-trimethoxysilylpropyl methacrylate were mixed in the weight ratio of 3:2:3:2:0.2. The resulting mixture was treated with nitrogen to replace the air, after which potassium persulfate was added and emulsion polymerization was carried out at 60° C. for 8 hours. After completion of the reaction, the concentration was adjusted with water to prepare an (inorganic fine particles)-coated organic fine particles dispersion F (40 wt %) in which magnesium aluminate metasilicate fine particles had been formed on the surfaces of the acrylic copolymer resin fine particles.

The (inorganic fine particles)-coated organic fine particles had a particle size of 0.08 μm and an inorganic fine particles content of 30 wt %.

A coating fluid for layer formation 8 prepared by diluting the (inorganic fine particles)-coated organic fine particles dispersion F with an equal amount of water was applied on the layer formation side of the above-mentioned sheet having on its one side the layer containing the photoreactive semiconductor and the film-forming inorganic fine particles, so that the amount of coating might be 10 g/m². Thus, a layer containing the (inorganic fine particles)-coated organic fine particles was separately laminated on the layer containing the photoreactive semiconductor and the film-forming inorganic fine particles, to obtain a photoreactive agent 10 for removing harmful materials.

EXAMPLE 11

The base paper made in Example 4 was impregnated with an aqueous solution of ammonium bromide, a flame retardant and dried.

Then, 5 parts by weight of Na-montmorillonite (Kunipia F, mfd. by Kunimine Kogyo K.K.) was added to 95 parts by weight of water as film-forming inorganic fine particles, and the resulting mixture was stirred until Na-montmorillonite particles disappeared. The above-mentioned base paper impregnated with ammonium bromide was impregnated with the thus obtained fluid containing the film-forming inorganic fine particles, so that the amount of coating might be 20 g/m² (the total on both sides). Thus, there was obtained a substrate in which a layer containing the film-forming inorganic fine particles had been formed on each side of the base paper containing the flame retardant.

With water were mixed 100 parts by weight of aluminum oxide (Higilite H-42M, mfd. by Showa Denko K.K.) as a carrier and 3.5 parts by weight of the same polycarboxylic acid ammonium salt (active ingredient 40 wt %) as used in Example 1, and they were dispersed with a DYNO-MILL as in Example 1 to prepare a 20 wt % carrier dispersion C.

To 50 parts by weight of the carrier dispersion C were added 50 parts by weight of the carrier dispersion A prepared in Example 2 and 100 parts by weight of the photoreactive semiconductor dispersion A prepared in Example 1, and the resulting mixture was thoroughly stirred to support the photoreactive semiconductor on the carriers.

To 200 parts by weight of the thus obtained (photoreactive semiconductor)-supporting carrier dispersion were added 20 parts by weight of colloidal silica (Snowtex UP, mfd. by Nissan Kagaku K.K.; 20 wt %) as film-forming inorganic fine particles and then 60 parts by weight of the (inorganic fine particles)-coated organic fine particles dispersion C prepared in the Example 5, and 20 parts by weight of water was added with stirring to prepare a coating fluid for layer formation 9 containing the photoreactive semiconductor, the (inorganic fine particles)-coated organic fine particles, the carriers and the film-forming inorganic fine particles [photoreactive semiconductor:(inorganic fine particles)-coated organic fine particles carriers:film-forming inorganic fine particles=5:6:5:2 in terms of solids].

The coating fluid for layer formation 9 was applied on the layer containing the film-forming inorganic fine particles on one side of the substrate, so that the amount of coating might be 30 g/m², whereby there was formed a layer containing the photoreactive semiconductor, the (inorganic fine particles)-coated organic fine particles, the carriers and the film-forming inorganic fine particles.

Then, the surfaces of the resulting sheet on which the layers containing at least film-forming inorganic fine particles had been formed were coated with a water repellent-containing liquid prepared by mixing equal amounts of a silicone type water repellent (TSW831, mfd. by Toshiba Silicon K.K.) and a catalyst (CW80, mfd. by Toshiba Silicon K.K.) and diluting the resulting mixture in 10 times with water, so that the amount of coating might be 0.2 g/m² (each side). The sheet was dried in a 80° C. hot-air dryer for 10 minutes, whereby a layer containing the water repellent was separately laminated on the layer containing the photoreactive semiconductor, the (inorganic fine particles)-coated organic fine particles, the carriers and the film-forming inorganic fine particles. Thus, a photoreactive agent 11 for removing harmful materials was obtained.

EXAMPLE 12

The sheet prepared in Example 7 by forming a layer containing a photoreactive semiconductor and film-forming inorganic fine particles on each side of a substrate was impregnated with the coating fluid for layer formation 8 containing (inorganic fine particles)-coated organic fine particles which had been prepared in Example 10 by mixing the (inorganic fine particles)-coated organic fine particles dispersion F (40 wt %) with an equal volume of water, so that the amount of coating might be 18 g/m² (the total on both sides). Thus, a layer containing the (inorganic fine particles)-coated organic fine particles was separately laminated on each layer containing the photoreactive semiconductor and the film-forming inorganic fine particles.

The surface of each layer containing the (inorganic fine particles)-coated organic fine particles of the sheet was impregnated with a 5 wt % aqueous dispersion of a silicone type water repellent (FZ-4658, mfd. by Nippon Unicar Co., Ltd.) so that the amount of coating might be 18 g/m² (the total on both sides), after which the sheet was dried in a 80° C. hot-air dryer. Thus, the layer containing the photoreactive semiconductor and the film-forming inorganic fine particles, the layer containing the (inorganic fine particles)-coated organic fine particles, and a layer containing the water repellent were separately laminated on each side in that order to obtain a photoreactive agent 12 for removing harmful materials.

COMPARATIVE EXAMPLE 1

With 50 parts by weight of an acrylic resin emulsion (2V-5011, mfd. by Kanebo NSC; 50 wt %) as organic fine particles was mixed 100 parts by weight of the photoreactive semiconductor dispersion A prepared in Example 1, to prepare a coating fluid for layer formation 10 containing the photoreactive semiconductor and the organic fine particles.

The surface of a PET film of 70 μm thickness was subjected as a substrate to corona treatment to be made hydrophilic, and was immediately and continuously coated with the coating fluid for layer formation 10 by means of a comma coater so that the amount of coating might be 15 g/m². Thus, there was obtained a photoreactive agent 13 for removing harmful materials which had a layer containing the photoreactive semiconductor and the organic fine particles.

COMPARATIVE EXAMPLE 2

An organic fine particles dispersion prepared by diluting a styrene/butadiene copolymer latex (Nipol LX119, mfd. by Nippon Zeon Co., Ltd.; 50 wt %) as organic fine particles with an equal volume of water was continuously applied on the layer formation side of the sheet prepared in Example 10 by forming a layer containing a photoreactive semiconductor and film-forming inorganic fine particles on a substrate, by means of a comma coater so that the amount of coating might be 15 g/m². Thus, a layer containing the other organic fine particles was separately laminated on the layer containing a photoreactive semiconductor and film-forming inorganic fine particles, to obtain a photoreactive agent 14 for removing harmful materials.

Measurement of the Ability to Remove Harmful Materials by Light

Each of the photoreactive agents 1 to 14 for removing harmful materials was cut into pieces 10 cm square, and pieces of each kind were placed in a 5.6-liter polyethylene container with their layer formation sides to a lamp, after which saturated acetaldehyde gas was introduced thereinto to adjust the acetaldehyde concentration in the container to 10 ppm.

The pieces of each of the photoreactive agents 1 to 14 for removing harmful materials were irradiated by a 6-W black lamp from a distance of 4 cm, and the acetaldehyde concentration in the container 5 minutes after the start of the irradiation was measured with a gas chromatographic apparatus equipped with an FID detector.

Evaluation of the Film Strength of the Layer Formed Peeling by a Tape:

A pressure-sensitive adhesive tape was attached to the layer formation side under a definite load, and after a definite time, the tape was peeled off and the degree of film peeling was estimated.

Peeling by Rubbing with a Finger:

The layer formation side was rubbed with a finger, after which the degree of film peeling was estimated.

Peeling by Washing with Water:

The layer formation side was exposed to tap water for a definite time, after which the degree of film peeling was estimated.

With respect to each of the above evaluation items, no peeling of the layer is expressed by ○, partial peeling of the layer by Δ, and substantially overall peeling of the layer by x.

Evaluation of Weather Resistance

The photoreactive agents 1 to 14 for removing harmful materials produced in the above were exposed to the sun for 5 days, after which the degree of their discoloration was estimated. No discoloration or discoloration undistinguishable in itself but distinguishable from the color before the exposure is expressed by ○, somewhat yellowing by Δ, and obvious yellowing by x.

In the same manner as above, the ability to remove harmful materials by light was measured for the photoreactive agents for removing harmful materials which had been exposed to the sun for 5 days. The results of the measurement and evaluation are also shown in Table 1.

TABLE 1

| | Removing agent No. | Ability to remove harmful materials by light[*1] | Film strength (peeling) | | | Weather resistance | |
| | | | Tape | Rubbing with a finger | Washing with water | Dis-coloration | Removing ability[*1] |
|---|---|---|---|---|---|---|---|
| Example 1 | 1 | 2.7 | ○ | ○ | ○ | ○ | 2.5 |
| Example 2 | 2 | 1.2 | ○ | ○ | ○ | ○ | 1.0 |
| Example 3 | 3 | 1.1 | ○ | ○ | ○ | ○ | 0.9 |
| Example 4 | 4 | 1.1 | Δ[*2] | ○ | ○ | ○ | 1.0 |
| Example 5 | 5 | 1.3 | ○ | ○ | ○ | ○ | 1.2 |
| Example 6 | 6 | 1.2 | ○ | ○ | ○ | ○ | 1.1 |
| Example 7 | 7 | 1.5 | ○ | ○ | ○ | ○ | 1.2 |
| Example 8 | 8 | 1.2 | ○ | ○ | ○ | ○ | 1.1 |
| Example 9 | 9 | 1.1 | ○ | ○ | ○ | ○ | 1.1 |
| Example 10 | 10 | 1.3 | ○ | ○ | ○ | ○ | 1.1 |
| Example 11 | 11 | 2.0 | ○ | ○ | ○ | ○ | 1.9 |
| Example 12 | 12 | 1.3 | ○ | ○ | ○ | ○ | 1.1 |

TABLE 1-continued

|  | Removing agent No. | Ability to remove harmful materials by light*1 | Film strength (peeling) | | | Weather resistance | |
|---|---|---|---|---|---|---|---|
|  |  |  | Tape | Rubbing with a finger | Washing with water | Discoloration | Removing ability*1 |
| Comparative Example 1 | 13 | 10.0 | ○ | ○ | ○ | x | 8.9 |
| Comparative Example 2 | 14 | 10.0 | ○ | ○ | ○ | Δ | 9.5 |

Note:
*1: the concentration (ppm) of acetaldehyde remaining 5 minutes after the light irradiation.
*2: peeling together with the substrate (paper layer).

As is clear also from Table 1, in the case of the photoreactive agents for removing harmful materials obtained by laminating at least a photoreactive semiconductor and (inorganic fine particles)-coated organic fine particles as a single layer or in that order, a coating film having practical strength and water resistance can be obtained by virtue of the (inorganic fine particles)-coated organic fine particles because organic fine particles are thermally fused together with one another through spaces among inorganic fine particles located on the surfaces of organic fine particles, to form a matrix in a three-dimensional manner.

When the photoreactive semiconductor is present together with the (inorganic fine particles)-coated organic fine particles in one and the same layer, inorganic fine particles are effectively located among organic fine particles capable of substantially forming a coating film. Accordingly, the organic fine particle component is hardly influenced by the photoreactive semiconductor, and structural pores are formed by the inorganic fine particles and the photoreactive semiconductor, so that the contact of harmful materials with the photoreactive semiconductor can be assured.

These facts indicate the following: over a long period of time, the organic fine particle component is not deteriorated (namely, not discolored) and the photoreactive agents for removing harmful materials retain satisfactory performance characteristics with almost no change in the ability to remove harmful materials by light.

By contrast, in the case of the photoreactive agent 13 for removing harmful materials which contains a photoreactive semiconductor and organic fine particles not coated with inorganic fine particles in one and the same layer, the organic fine particles gave a coating film having practical strength and water resistance, but the photoreactive semiconductor was enveloped by the organic fine particles and hence remarkably inhibited from coming into contact with harmful materials. Therefore, the ability to remove harmful materials by light was greatly deteriorated and moreover the coating film was yellowed and deteriorated owing to marked oxidative decomposition by the photoreactive semiconductor.

In the case of the photoreactive agent 14 for removing harmful materials which was obtained by laminating a photoreactive semiconductor and organic fine particles not coated with inorganic fine particles in that order, a coating film formed by the inorganic fine particles completely covered a layer containing the photoreactive semiconductor, so that the contact of the photoreactive semiconductor with harmful materials was broken off. Therefore, the photoreactive agent 14 for removing harmful materials had no ability to remove harmful materials by light.

EXAMPLE 13

Hydrated titanium oxide was obtained by hydrolysis with heating of titanyl sulfate, an intermediate product in the conventional production process of titanium oxide by sulfuric acid method. The hydrated titanium oxide was washed with an aqueous sodium hydroxide solution and then peptized with hydrochloric acid to obtain a milk-white and semitransparent liquid containing titanium oxide (pH 1.2). The titanium oxide-containing liquid was fed to a high-shear mixer, after which the pH of the liquid was slowly increased to 4 by slowly dropping thereinto an aqueous alkali solution with high-speed stirring, and the stirring was continued for another 20 minutes to obtain a photoreactive semiconductor dispersion B.

Using a dip-type impregnating apparatus, the substrate prepared in Example 4 was passed through the photoreactive semiconductor dispersion B while dipping the substrate therein, whereby there was obtained a sheet in which layers containing the photoreactive semiconductor had been formed equally on both sides, respectively, of the substrate, so that the amount of coating might be about 30 g/m$^2$ (the total on both sides).

When the surface of the sheet having the layers containing the photoreactive semiconductor was rubbed with a finger, powder sticked to the finger and film peeling was caused.

The surfaces of both layers containing the photoreactive semiconductor of the sheet having the layers containing the photoreactive semiconductor were coated with the same colloidal alumina as used as film-forming inorganic fine particles in Example 10, so that the amount of coating might be 9 g/m$^2$ (each side) in terms of $Al_2O_3$. After drying with hot air, the sheet was dried at 40° C. under reduced pressure for another 2 hours in a vacuum dryer to obtain a laminated sheet in which a layer containing the film-forming inorganic fine particles had been separately laminated on each layer containing the photoreactive semiconductor.

When the surface of the laminated sheet was rubbed with a finger, neither sticking of powder or the like nor film peeling was observed. However, when water was dropped on the sheet and the sheet was rubbed with a finger, no change was immediately caused but both the layer containing the film-forming inorganic fine particles and the layer containing the photoreactive semiconductor were destroyed before long to expose the surface of the substrate.

In addition, the surfaces of both layers containing the film-forming inorganic fine particles of the laminated sheet were coated with the same 5 wt % aqueous silicone type water repellent dispersion as used in Example 12, so that the amount of coating might be 0.2 g/m$^2$ (each side). The laminated sheet was dried at 80° C. for 10 minutes in a hot-air dryer to obtain a photoreactive agent 15 for removing harmful materials in which the layer containing the photoreactive semiconductor, the layer containing the film-forming inorganic fine particles and a layer containing the water repellent had been separately laminated on each side in that order.

When the surface of the photoreactive agent 15 for removing harmful materials was rubbed with a finger, neither sticking of powder or the like nor film peeling was observed. When water was dropped on the removing agent 15 and the sheet was inclined, waterdrops slipped off the sheet easily, namely, the removing agent 15 exhibited a satisfactory water repellency. When water was again dropped on the removing agent 15 and after a while a portion corresponding to waterdrops was rubbed with a paper wiper, neither sticking of powder or the like nor film peeling was observed, namely, the removing agent 15 had satisfactory water-resistant coating films.

COMPARATIVE EXAMPLE 3

The silicone type water repellent dispersion prepared in Example 12 was applied on the surfaces of both layers containing the photoreactive semiconductor of the sheet having the layers containing the photoreactive semiconductor which had been produced in Example 13, so that the amount of coating might be 0.2 g/m$^2$ (each side) as in Example 13. The sheet was dried at 80° C. for 10 minutes in a hot-air dryer to obtain a photoreactive agent 16 for removing harmful materials in which the layer containing the water repellent had been separately laminated on each layer containing the photoreactive semiconductor.

As in Example 13, when water was dropped on the photoreactive agent 16 for removing harmful materials and the sheet was inclined, waterdrops slipped off the sheet easily, namely, the removing agent 16 exhibited a satisfactory water repellency. But, water was again dropped on the removing agent 16 and after a while a portion corresponding to waterdrops was rubbed with a paper wiper, the layer containing the photoreactive semiconductor was immediately peeled.

EXAMPLE 14

An aqueous liquid of a fluorine-containing water repellent (Dickgard F-400, mfd. by Dainippon Ink and Chemicals, Inc.) was applied on the surfaces of both layers containing film-forming inorganic fine particles of the laminated sheet prepared in Example 13 by separately laminating the layer containing the film-forming inorganic fine particles on each layer containing a photoreactive semiconductor, so that the amount of coating might be 0.3 g/m$^2$ (each side). The laminated sheet was dried at 80° C. for 10 minutes in a hot-air dryer to obtain a photoreactive agent 17 for removing harmful materials in which the layer containing the photoreactive semiconductor, the layer containing the film-forming inorganic fine particles and a layer containing the water repellent had been separately laminated on each side in that order.

As in Example 13, when the surface of the photoreactive agent 17 for removing harmful materials was rubbed with a finger, neither sticking of powder or the like nor film peeling was observed. When water was dropped on the removing agent 17 and the sheet was inclined, waterdrops slipped off the sheet easily, namely, the removing agent 17 exhibited a satisfactory water repellency. When water was again dropped on the removing agent 17 and after a while a portion corresponding to waterdrops was rubbed with a paper wiper, neither sticking of powder or the like nor film peeling was observed, namely, the removing agent 17 had satisfactory water-resistant coating films as in Example 13.

EXAMPLE 15

A 24:1 (by weight) mixture of colloidal silica (Snowtex-XL, mfd. by Nissan Kagaku K.K.) as film-forming inorganic fine particles and the same silicone type water repellent as used in Example 12 was applied on the surfaces of both layers containing the photoreactive semiconductor of the sheet having the layers containing the photoreactive semiconductor which had been prepared in Example 13, so that the amount of coating might be 12 g/m$^2$ (each side). After drying with hot air, the sheet was dried at 40° C. under reduced pressure for another 2 hours in a vacuum dryer to obtain a photoreactive agent 18 for removing harmful materials in which a layer containing the film-forming inorganic fine particles and the water repellent had been separately laminated on each layer containing the photoreactive semiconductor.

As in Example 13, when the surface of the photoreactive agent 18 for removing harmful materials was rubbed with a finger, neither sticking of powder or the like nor film peeling was observed. When water was dropped on the removing agent 18 and the sheet was inclined, waterdrops slipped off the sheet easily, namely, the removing agent 18 exhibited a satisfactory water repellency. When water was again dropped on the removing agent 18 and after a while a portion corresponding to waterdrops was rubbed with a paper wiper, neither sticking of powder or the like nor film peeling was observed, namely, the removing agent 18 had satisfactory water-resistant coating films as in Example 13.

EXAMPLE 16

Colloidal silica (Adelite AT-20S, mfd. by Asahi Denka Co., Ltd.) was applied as film-forming inorganic fine particles on both sides of the substrate prepared in Example 4, so as to adjust the amount of coating to 8 g/m$^2$ (each side), and was dried with hot air. On the resulting layers, the photoreactive semiconductor dispersion B prepared in Example 13 was applied so as to adjust the amount of coating to 15 g/m$^2$ (each side), whereby the layers containing the photoreactive semiconductor were formed. These layers were dried with hot air to obtain a laminated sheet in which the layer containing the photoreactive semiconductor had been separately laminated on each layer containing film-forming inorganic fine particles.

A mixed dispersion of synthetic smectite (SWF, mfd. by Coop Chemical K.K.) as film-forming inorganic fine particles and colloidal silica (Cataloid SI-45P, mfd. by Shokubai Kasei Kogyo K.K.) in the ratio of 1:2 by weight (the weight of the colloidal silica is in terms of $SiO_2$) is applied on the surfaces of both layers containing the photoreactive semiconductor of the laminated sheet, so as to adjust the amount of coating to 10 g/m$^2$ (each side), and was dried with hot air and then at 40° C. under reduced pressure for another 2 hours in a vacuum dryer. Thus, there was obtained a laminated sheet in which the layer containing the film-forming inorganic fine particles, the layer containing the photoreactive semiconductor and a layer containing the other film-forming inorganic fine particles had been separately laminated on each side in that order.

When the surface of the laminated sheet was rubbed with a finger, neither sticking of powder or the like nor film peeling was observed. However, when water was dropped on the sheet and the sheet was rubbed with a finger, no change was immediately caused but both the layer containing the film-forming inorganic fine particles and the layer containing the photoreactive semiconductor were destroyed before long.

The mixed dilution of a silicone type water repellent and a catalyst prepared in Example 11 was applied on the surfaces of both uppermost layers containing the film-forming inorganic fine particles of the laminated sheet, so as to adjust the amount of coating to 0.2 g/m² (each side), and was dried at 80° C. for 10 minutes in a hot-air dryer. Thus, there was obtained a photoreactive agent 19 for removing harmful materials in which the layer containing the film-forming inorganic fine particles, the layer containing the photoreactive semiconductor, the layer containing the other film-forming inorganic fine particles, and a layer containing the water repellent had been separately laminated on each side in that order.

As in Example 13, when the surface of the photoreactive agent 19 for removing harmful materials was rubbed with a finger, neither sticking of powder or the like nor film peeling was observed. When water was dropped on the removing agent 19 and the sheet was inclined, waterdrops slipped off the sheet easily, namely, the removing agent 19 exhibited a satisfactory water repellency. When water was again dropped on the removing agent 19 and after a while a portion corresponding to waterdrops was rubbed with a paper wiper, neither sticking of powder or the like nor film peeling was observed, namely, the removing agent 19 had satisfactory water-resistant coating films as in Example 13.

EXAMPLE 17

To water containing a very small amount of a surfactant (decaglyceryl isostearate) were added 60 parts by weight of titanium oxide (ST-31, mfd. by Ishihara Sangyo Kaisha, Ltd.; specific surface area 220 m²/g) and 40 parts by weight of the same catalyst as used in Example 2, and they are mixed and stirred to prepare a (photoreactive semiconductor)-supporting carrier dispersion.

The nonwoven fabric prepared in Example 6 was subjected to corona treatment and then treated with the (photoreactive semiconductor)-supporting carrier dispersion by means of a dip-type impregnating apparatus while dipping the nonwoven fabric in the dispersion as in Example 13, whereby layers containing the photo-reactive semiconductor and the carrier were equally formed on both sides, respectively, of the nonwoven fabric so that the amount of coating might be 50 g/m² (the total on both sides). The thus treated nonwoven fabric was dried with hot air to obtain a sheet having a layer containing the photoreactive semiconductor and the carrier.

When the sheet having a layer containing the photoreactive semiconductor and the carrier was rubbed with a finger, powder sticked to the finger and film peeling was caused.

A liquid prepared by mixing colloidal alumina (Aluminasol-100, mfd. by Nissan Kagaku Kogyo K.K.) as film-forming inorganic fine particles, colloidal silica (Snowtex-YL, mfd. by Nissan Kagaku Kogyo K.K.) and a silicone type water repellent (UM-120, mfd. by Toshiba Silicon K.K.) in the weight ratio of 20:10:1 was applied on both surfaces of the sheet having a layer containing the photoreactive semiconductor and the carrier, so as to adjust the amount of coating to 12 g/m² (each side). After drying with hot air, the sheet was dried at 40° C. under reduced pressure for another 2 hours in a vacuum dryer to obtain a photoreactive agent 20 for removing harmful materials in which a layer containing the film-forming inorganic fine particles and the water repellent had been separately laminated on each layer containing the photoreactive semiconductor and the carrier.

As in Example 13, when the surface of the photoreactive agent 20 for removing harmful materials was rubbed with a finger, neither sticking of powder or the like nor film peeling was observed. When water was dropped on the removing agent 20 and the sheet was inclined, waterdrops slipped off the sheet easily. When water was again dropped on the removing agent 20 and after a while a portion corresponding to waterdrops was rubbed with a paper wiper, neither sticking of powder or the like nor film peeling was observed, namely, the removing agent 20 had satisfactory water-resistant coating films as in Example 13.

COMPARATIVE EXAMPLE 4

Aluminosilicate (Silton AMT-08, composed mainly of alumina and silica and having no film-forming properties; mfd. by Mizusawa Industrial Chemical, Ltd.) and the mixture of a silicone type water repellent and a catalyst prepared in Example 11 was added to water containing a very small amount of a surfactant (decaglyceryl isostearate), in the weight ratio of 30:1, and they were stirred and mixed. The resulting mixture was applied on both sides of the sheet having layers containing a photoreactive semiconductor and a carrier which had been prepared in Example 17, so as to adjust the amount of coating to 12 g/m² (each side) as in Example 17. The sheet was dried with hot air to obtain a photoreactive agent 21 for removing harmful materials which had on each side the layer containing the photoreactive semiconductor and the carrier and a layer containing the inorganic fine particles and the water repellent.

As in Example 13, when water was dropped on the photoreactive agent 21 for removing harmful materials and the sheet was inclined, waterdrops slipped off the sheet easily, namely, the removing agent 21 exhibited a satisfactory water repellency. But, water was again dropped on the removing agent 21 and after a while a portion corresponding to waterdrops was rubbed with a paper wiper, the layer containing the photoreactive semiconductor and the carrier was immediately peeled as in Comparative Example 3.

EXAMPLE 18

To water were added 40 parts by weight of poly(ethylene terephthalate) fiber with a fineness of 0.15 d and fiber length of 7.5 mm (mfd. by Teijin Ltd.) and polyester type flame-retardant fiber with a fineness of 1.5 d and fiber length of 15 mm (Trevira CS, mfd. by Teijin Ltd.) together with a surfactant (hexaglyceryl laurate), and they were vigorously stirred by means of a pulper until bundles of fibers disappeared. The resulting mixture was diluted with water and then increased in viscosity by adding an aqueous polyacrylamide solution with mild stirring by means of an agitator, and the stirring was continued to obtain a slurry of uniformly dispersed fibers. Using the slurry, a web was prepared with a cylinder paper machine so as to have a basis weight of 80 g/m².

The web was set on a stainless steel wire net substrate of about 100 mesh and a stream of water was jetted from above the web to entangle fibers on the right and reverse sides once for each. After completion of the entangling, the web was dried with air-through dryer to obtain nonwoven fabric of fibers entangled by water stream.

The nonwoven fabric was treated with the 5 wt % film-forming inorganic fine particles dispersion prepared in Example 11, by means of a dip-type impregnating apparatus while dipping the nonwoven fabric in the dispersion, whereby layers containing the film-forming inorganic fine particles were equally formed on both sides, respectively, of the nonwoven fabric so that the amount of coating might be 15 g/m² (the total on both sides). Then, the nonwoven fabric was dried with hot air.

The photoreactive semiconductor dispersion A prepared in Example 1 was applied on the surfaces of both layers containing the film-forming inorganic fine particles, so as to adjust the amount of coating to 15 g/m² (each side), and was dried with hot air to obtain a laminated sheet in which a layer containing the photoreactive semiconductor had been separately laminated on each layer containing the film-forming inorganic fine particles.

When the surface of the laminated sheet was rubbed with a finger, powder sticked to the finger and film peeling was caused.

Colloidal silica (Snowtex-20L, mfd. by Nissan Kagaku Kogyo K.K.) was applied as film-forming inorganic fine particles on the surfaces of both layers containing the photoreactive semiconductor of the laminated sheet, to adjust the amount of coating to 11 g/m² (each side). After drying with hot air, the laminated sheet was dried at 40° C. under reduced pressure for another 2 hours in a vacuum dryer to obtain a laminated sheet in which the layer containing the film-forming inorganic fine particles, the layer containing the photoreactive semiconductor, and a layer containing the other film-forming inorganic fine particles had been separately laminated on each side in that order.

When the surface of the laminated sheet was rubbed with a finger, neither sticking of powder or the like nor film peeling was observed. However, when water was dropped on the sheet and the sheet was rubbed with a finger, no change was immediately caused but both the layer containing the film-forming inorganic fine particles and the layer containing the photoreactive semiconductor were destroyed before long.

In addition, a 5 wt % aqueous dispersion of a silicone type water repellent (FZ-4158, mfd. by Nippon Unicar Co., Ltd.) was applied on the surfaces of both uppermost layers containing film-forming inorganic fine particles of the laminated sheet, to adjust the amount of coating to 0.3 g/m² (each side). Then, the laminated sheet was dried at 80° C. for 10 minutes in a hot-air dryer to obtain a photoreactive agent 22 for removing harmful materials in which the layer containing the film-forming inorganic fine particles, the layer containing the photoreactive semiconductor, the layer containing the other film-forming inorganic fine particles, and a layer containing the water repellent had been separately laminated on each side in that order.

As in Example 13, when the surface of the photoreactive agent 22 for removing harmful materials was rubbed with a finger, neither sticking of powder or the like nor film peeling was observed. When water was dropped on the removing agent 22 and the sheet was inclined, waterdrops slipped off the sheet easily. When water was again dropped on the removing agent 22 and after a while a portion corresponding to waterdrops was rubbed with a paper wiper, neither sticking of powder or the like nor film peeling was observed namely, the removing agent 22 had satisfactory water-resistant coating films as in Example 13.

Each of the photoreactive agents 15 to 22 for removing harmful materials which had been produced in Examples 13 to 18 and Comparative Examples 3 and 4 and the sheet having a layer containing a photoreactive semiconductor and a carrier (expressed in the word "sheet" in Table 2) which had been produced in Example 17 was cut into pieces 10 cm square. The pieces of each kind were horizontally held at a height of 10 cm from the bottom of a hermetically sealable container (20 cm×20 cm×20 cm in the clear) having a dull-black inside. Acetaldehyde, a typical malodorous compound was introduced into each sealable container to adjust its concentration therein to about 400 ppm, and the container was irradiated by a 6-W black lamp for a definite time, after which the residual acetaldehyde concentration in the container was measured. The results obtained are shown in Table 2.

The water resistance was evaluated by visually estimating the degree of change in waterdrops formed by dropping, as described above, water on the surface of the water repellent-containing layer of each of the photoreactive agents 15 to 22 for removing harmful materials, or the degree of change in the coating film which came into contact with the waterdrops. In Table 2, the "Inclination" column shows the degree of removal of waterdrops by the inclination of each sheet after water dropping, and the "Rubbing-off" column shows the degree of sticking of powder or the like or film peeling, which was caused by dropping water and after a while, rubbing a portion corresponding to waterdrops with a paper wiper. The sheet having a layer containing a photoreactive semiconductor and a carrier which had been produced in Example 17 was not subjected to the water resistance test because its coating film was brittle even in a dry state as described above. The results of the tests are also shown in Table 2.

TABLE 2

|  | Removing agent No. | Residual acetaldehyde concentration (ppm) | Water resistance | |
| --- | --- | --- | --- | --- |
|  |  |  | Inclination | Rubbing-off |
| Example 13 | 15 | 50 | ◎ | ◎ |
| Comparative Example 3 | 16 | 50 | ◎ | x |
| Example 14 | 17 | 55 | ◎ | ◎ |
| Example 15 | 18 | 50 | ◎ | ○ |
| Example 16 | 19 | 60 | ◎ | ◎ |
| Example 17 | 20 | 40 | ○ | ◎ |
| Comparative Example 4 | 21 | 40 | ○ | x |
| Example 18 | 22 | 40 | ○ | ◎ |
|  | sheet | 30 | — | — |

Note: Water resistance was rated as follows in a decending scale: ◎, ○, Δ and x.

The acetaldehyde-removing ability was measured also for the substrate (prepared in Example 4) used in Example 13, to find that the residual acetaldehyde concentration was 325 ppm. From this fact and Table 2, it can be said that all of the products having at least a layer containing a photoreactive semiconductor are effective as an agent for removing harmful materials, irrespective of properties of a substrate and coating inorganic fine particles and the presence of a coating because the products markedly decreased acetaldehyde.

However, when either a layer containing film-forming inorganic fine particles or a layer containing a water repellent was not formed on a layer containing a photoreactive semiconductor, the film strength or the water resistance, respectively, was poor, so that a coating film fell off easily, namely, only a result undesirable in practice was obtained.

Compared with such products, in the present inventive removing agents obtained by forming a layer containing a film-forming inorganic fine particles and a layer containing a water repellent on a layer containing a photoreactive semiconductor (the photoreactive agents 15, 17, 18, 19, 20 and 22 for removing harmful materials), coating is achieved with good water resistance without hindering the contact of harmful materials with the layer containing a photoreactive semiconductor. Therefore, as is clear from Table 2, these removing agents are excellent in not only ability to decompose acetaldehyde, a harmful material but also water resistance.

Furthermore, the layer containing a film-forming inorganic fine particles according to the present invention is not affected by oxidative decomposition by the photoreactive semiconductor, so that a coating film of the inorganic fine particles is not deteriorated over a long period of time. Therefore, excellent results (no deterioration of the water resistance) were obtained also in a test for film strength after an extended period which was carried out by continuous irradiation by a black lamp.

As explained above, the photoreactive agent for removing harmful materials of the present invention can be easily produced and can be allowed to exhibit an excellent photocatalytic effect, regardless of a material for its substrate and the shape of the substrate. As a light source, there may be used not only the black lamp used in Examples but also the sun, a fluorescent lamp, etc. which permit irradiation with ultraviolet light. When the substrate of the photoreactive agent for removing harmful materials is paper or nonwoven fabric, harmful materials can easily be removed by personally cutting the photoreactive agent to a suitable size and merely placing the resulting piece in a place where the removal of harmful materials is desired. Therefore, the photoreactive agent for removing harmful materials can be used easily and efficiently, depending on the degree of malodor and a setting place.

What is claimed is:

1. A photoreactive agent for removing harmful materials, wherein said harmful materials are removed by light and said photoreactive agent is water resistant, which comprises a substrate and a layer containing a photoreactive semiconductor and organic fine particles each coated with inorganic fine particles, wherein said inorganic fine particles have no photoreactivity, and said layer is formed on at least one side of the substrate and the inorganic particles are arranged between the photoreactive semiconductor and the organic fine particles, whereby the organic fine particles avoid the strong influence of oxidative decomposition by the photoreactive semiconductor and wherein oxidation of the organic fine particles is prevented, harmful substances are adsorbed without reducing the surface area of the photoreactive semiconductor and harmful substances are decomposed without deteriorating the function of the photoreactive semiconductor.

2. A photoreactive agent for removing harmful materials according to claim 1, which further comprises a layer containing a water repellent on the layer containing organic fine particles coated with inorganic fine particles.

3. A photoreactive agent for removing harmful materials according to claim 1, wherein the inorganic fine particle component of the organic fine particles coated with inorganic fine particles is a metal oxide.

4. A photoreactive agent for removing harmful materials according to claim 1, which further comprises a layer containing film-forming inorganic fine particles between the substrate and the layer containing a photoreactive semiconductor.

5. A photoreactive agent for removing harmful materials according to claim 1, wherein the layer containing a photoreactive semiconductor further contains a carrier.

6. A photoreactive agent for removing harmful materials according to claim 5, wherein the carrier is a hydrated oxide capable of releasing water owing to heat.

7. A photoreactive agent for removing harmful materials according to claim 1, wherein the substrate contains a flame retardant.

8. A photoreactive agent for removing harmful materials, wherein said harmful materials are removed by light and said photoreactive agent is water resistant, which comprises a substrate, a layer containing a photoreactive semiconductor and a layer containing organic fine particles coated with inorganic fine particles, wherein said inorganic fine particles have no photoreactivity, and said layers are formed in that order on at least one side of the substrate and the inorganic particles are arranged between the photoreactive semiconductor and the organic fine particles, whereby the organic fine particles avoid the strong influence of oxidative decomposition by the photoreactive semiconductor and wherein oxidation of the organic fine particles is prevented, harmful substances are adsorbed without reducing the surface area of the photoreactive semiconductor and harmful substances are decomposed without deteriorating the function of the photoreactive semiconductor.

9. A photoreactive agent for removing harmful materials according to claim 8, which further comprises a layer containing a water repellent on the layer containing organic fine particles coated with inorganic fine particles.

10. A photoreactive agent for removing harmful materials according to claim 8, wherein the inorganic fine particle component of the organic fine particles coated with inorganic fine particles is a metal oxide.

11. A photoreactive agent for removing harmful materials according to claim 8, which further comprises a layer containing film-forming inorganic fine particles between the substrate and the layer containing a photoreactive semiconductor.

12. A photoreactive agent for removing harmful materials according to claim 8, wherein the layer containing a photoreactive semiconductor further contains a carrier.

13. A photoreactive agent for removing harmful materials according to claim 8, wherein the substrate contains a flame retardant.

14. A photoreactive agent for removing harmful materials, wherein said harmful materials are removed by light and said photoreactive agent is water resistant, which comprises a substrate, a layer containing a photoreactive semiconductor and a layer containing film-forming inorganic fine particles, wherein said inorganic fine particles have no photoreactivity, and a water repellent, which layers are formed in that order on at least one side of the substrate.

15. A photoreactive agent for removing harmful materials according to claim 14, which further comprises a layer containing film-forming inorganic fine particles between the substrate and the layer containing a photoreactive semiconductor.

16. A photoreactive agent for removing harmful materials according to claim 14, wherein the layer containing a photoreactive semiconductor further contains a carrier.

17. A photoreactive agent for removing harmful materials according to claim 16, wherein the carrier is a hydrated oxide capable of releasing water owing to heat.

18. A photoreactive agent for removing harmful materials according to claim 14, wherein the substrate contains a flame retardant.

19. A photoreactive agent for removing harmful materials, wherein said harmful materials are removed by light and said photoreactive agent is water resistant, which comprises a substrate, a layer containing a photoreactive semiconductor, a layer containing film-forming inorganic fine particles, wherein said inorganic fine particles have no photoreactivity, and a layer containing a water repellent, which layers are formed in that order on at least one side of the substrate.

20. A photoreactive agent for removing harmful materials according to claim 19, which further comprises a layer containing film-forming inorganic fine particles between the substrate and the layer containing a photoreactive semiconductor.

21. A photoreactive agent for removing harmful materials according to claim 19, wherein the layer containing a photoreactive semiconductor further contains a carrier.

22. A photoreactive agent for removing harmful materials according to claim 19, wherein the substrate contains a flame retardant.

* * * * *